United States Patent
Dumesic et al.

(10) Patent No.: US 7,671,246 B2
(45) Date of Patent: *Mar. 2, 2010

(54) METHOD TO MAKE ALKANES AND SATURATED POLYHYDROXY COMPOUNDS FROM CARBONYL COMPOUNDS

(75) Inventors: James A. Dumesic, Verona, WI (US); George W. Huber, Belchertown, MA (US); Juben N. Chheda, Houston, TX (US); Christopher J. Barrett, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 416 days.

This patent is subject to a terminal disclaimer.

(21) Appl. No.: 11/682,021

(22) Filed: Mar. 5, 2007

(65) Prior Publication Data

US 2008/0058563 A1 Mar. 6, 2008

Related U.S. Application Data

(60) Provisional application No. 60/779,578, filed on Mar. 6, 2006.

(51) Int. Cl.
*C07C 1/00* (2006.01)
(52) U.S. Cl. .................. 585/240; 585/252; 585/260; 585/702; 585/899
(58) Field of Classification Search .............. 585/240, 585/252, 260, 265, 702, 899; 549/488, 489, 549/468
See application file for complete search history.

(56) References Cited

U.S. PATENT DOCUMENTS

| | | | |
|---|---|---|---|
| 4,154,744 A | * | 5/1979 | Hamada et al. ............ 549/483 |
| 5,300,654 A | | 4/1994 | Nakajima et al. |
| 5,583,263 A | | 12/1996 | Muthusamy et al. |
| 5,840,992 A | | 11/1998 | Kido et al. |
| 2004/0138510 A1 | | 7/2004 | Kramarz et al. |
| 2005/0004401 A1 | | 1/2005 | Barnicki et al. |

FOREIGN PATENT DOCUMENTS

| | | |
|---|---|---|
| JP | 62 192 335 | 8/1987 |
| WO | WO 00/00456 A1 | 1/2000 |
| WO | WO 01/02330 A1 | 1/2001 |

OTHER PUBLICATIONS

Aramendia et al. (2004) Synthesis and textural-structural characterization of magnesia, magnesia-titania and magnesia-zirconia catalysts, *J. Mol. Catalysis A: Chemical* 218:81-90.

(Continued)

*Primary Examiner*—N. Bhat
(74) *Attorney, Agent, or Firm*—Joseph T. Leone, Esq.; DeWitt Ross & Stevens S.C.

(57) ABSTRACT

A catalytic process for converting biomass-derived carbohydrates to liquid alkanes, alkenes, and/or ethers is described. The process uses combinations of self- and crossed-aldol condensation reactions, dehydration reactions, and hydrogenation reactions, over specified metal-containing catalysts, to yield alkane, alkene, and ether products from carbohydrate reactants.

28 Claims, 12 Drawing Sheets

OTHER PUBLICATIONS

Aramendia et al. (2004) Magnesium-ctontaining mixed oxides as basic catalysts: base characterization by carbon dioxide TPD-MS and test reactions, *Colloids & Surfaces A: Physicochem: Eng. Aspects* 234:17-25.

Barrett et al. (2006) Single-reactor process for sequential aldol-condensation and hydrogentation of biomass-derived compounds in water, *Applied Catalysis B: Environmental* 66:111-118.

Climent et al. (2004) Activated hydrotalcites as catalysts for the synthesis of chalcones of pharmaceutical interest, *J. Catalysis* 221:474-482.

Córdova et al. (2002) Direct organocatalytic aldol reactions in buffered aqueous media, *Chem. Commun.* 3024-3025.

Gutsche et al. (1967) *Amer. Chem. Soc. 89*:5.

Hyodonckx et al. (2007) *Ullmann's Encyclopedia of Industrial Chemistry* XP002449065, paragraph [02.2].

Huber et al. (2005) Production of Liquid Alkanes by Aqueous-Phase Processing of Biomass-Derived Carbohydrates, *Science Reprint*, 308:1446-1450.

Liu et al. (2003), L-Proline catalyzed asymmetric aldol reactions of protected hydroxyacetone, *National Laboratory of Applied Organic Chemistry*, Institute of Organic Chemistry, Lanzhou University, Lanzhou, P.R. China.

Roelefs et al. (2001) Condensation of citral and ketones using activated hydrotalcite catalysts, *Catalysis Letters* 74(1-2):91-94.

Salmi et al. (1999) Development of clean technology, *Green Chemistry* 283-287.

Serra-Holm et al. (2000) Aldolization of butyraldehyde with formaldehyde over a commercial anion-exchange resin—kinetics and selectivity aspects, *Applied Catalysis A: General* 198:207-221.

Serra-Holm et al. (2001) Comparison of Activity and Selectivity of Weakly Basic Anion-Exchange Catalysts for the Aldolization of Butyraldehyde with Formaldehyde, *Organic Process Research & Development*, 5:368-375.

Shigemasa et al. (1994) Synthesis of *threo*- and *erythro*-3-Pentulose by Aldol Type Reaction in Water, *Tetrahedron Letters*, vol. 35, No. 8, pp. 1263-1266.

Wang et al. (2004) Environmentally Friendly and Efficient Process for the Preparation of β-Hydroxyl Ketones, *Organic Process Research & Development*, 8:18-21.

\* cited by examiner

FIG. 2A
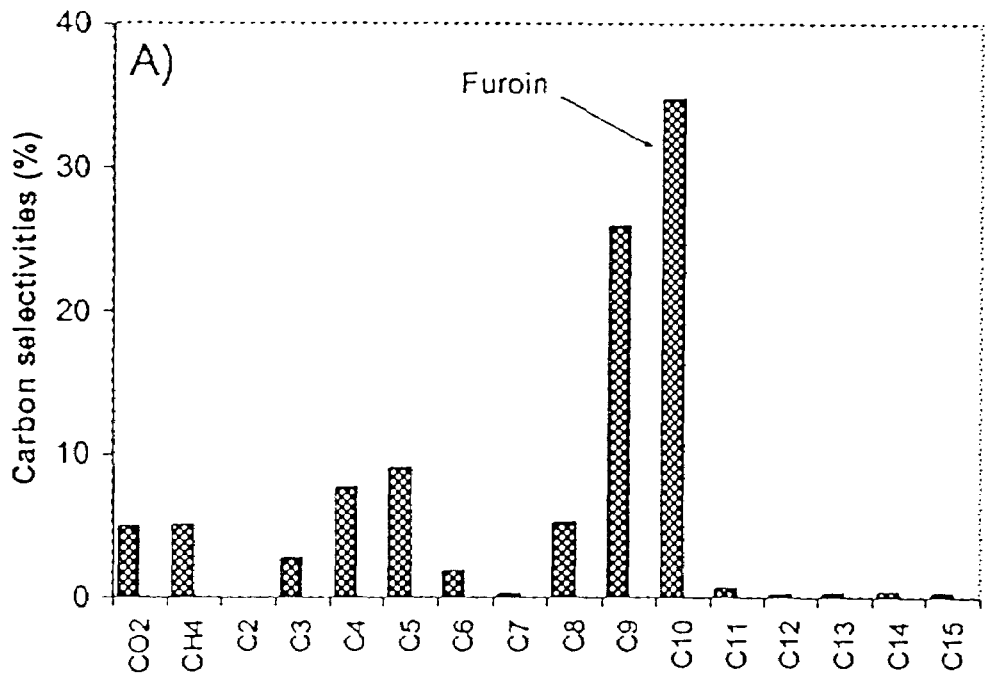
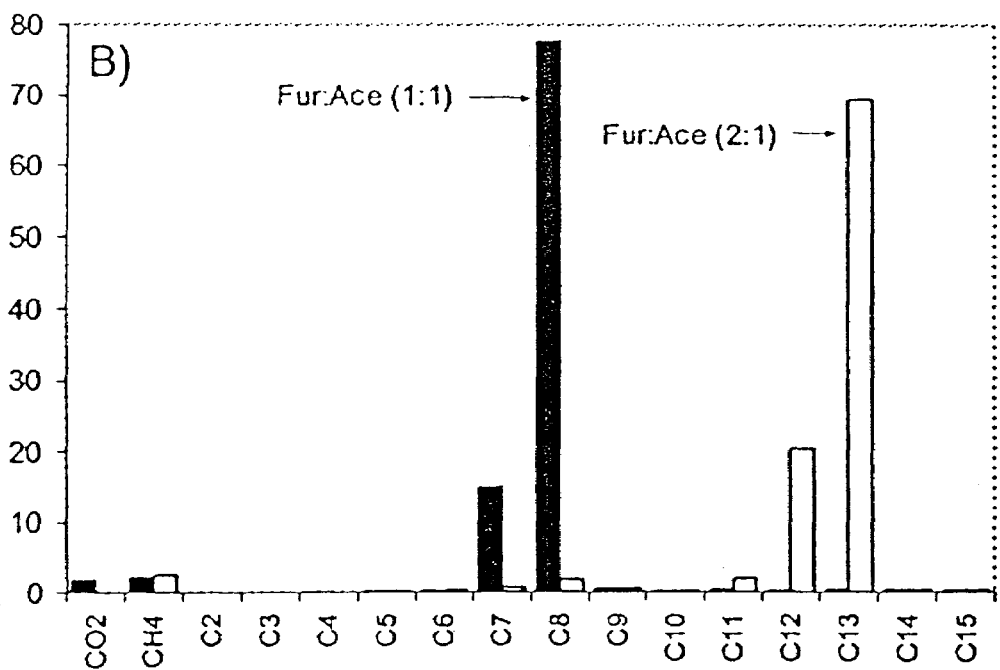
FIG. 2B

FIG. 2C
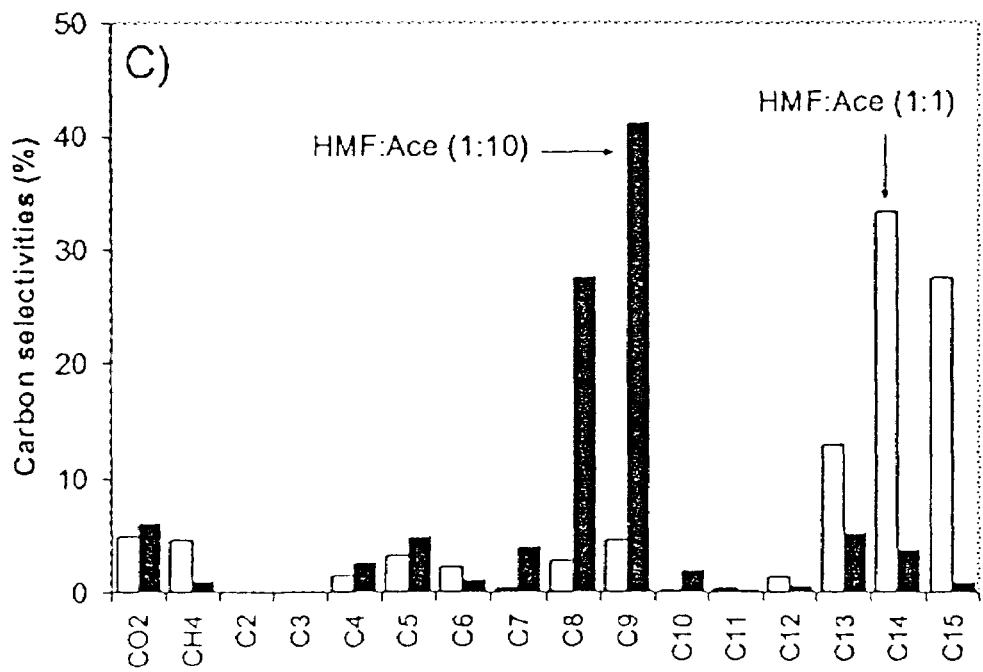
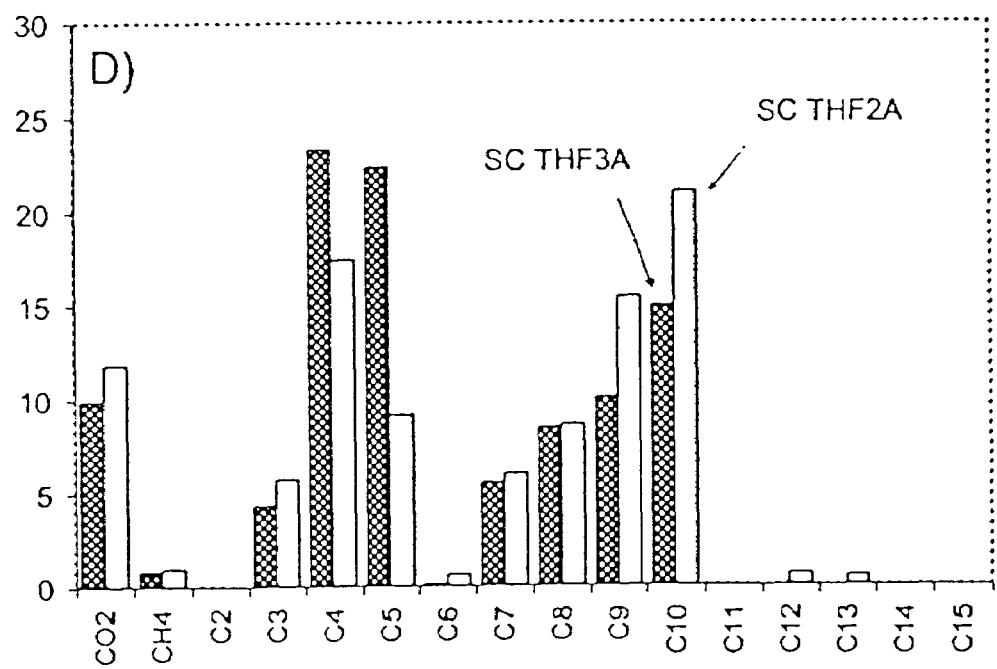
FIG. 2D

METHOD TO MAKE ALKANES AND SATURATED POLYHYDROXY COMPOUNDS FROM CARBONYL COMPOUNDS

CROSS-REFERENCE TO RELATED APPLICATIONS

Priority is hereby claimed to provisional application Ser. No. 60/779,578, filed Mar. 6, 2006, and incorporated herein by reference.

FEDERAL FUNDING STATEMENT

This invention was made with government support awarded by the following agencies: DOE: DE-FG02-84ER13183 and NSF: 0327959. The United States has certain rights in this invention.

FIELD OF THE INVENTION

The invention is directed to catalysts and reactions for converting carbohydrates (preferably biomass-derived carbohydrates) into liquid (e.g. $C_6$ to $C_{15}$) alkanes, alkenes, aldols, and the like, or mixtures of gas/liquid $C_1$ to $C_{15}$ alkanes, alkenes, aldols, and the like. The preferred embodiment is a multi-stage process comprising an acid-catalyzed dehydration of biomass-derived carbohydrates, followed by an aldol condensation reaction using a stable catalyst comprising magnesium, zirconium, and oxygen (and optionally palladium) to yield large organic compounds. These organic compounds are then converted into long-chain alkanes by dehydration/hydrogenation.

BACKGROUND

In an aldol condensation reaction, an aldehyde or ketone, one of which must have a hydrogen atom alpha to the carbonyl, react to form a β-hydroxy aldehyde or a β-hydroxy ketone (hereinafter collectively referred to as "β-hydroxy carbonyls"). A principal benefit of the aldol reaction is that it forms new carbon-carbon bonds. The initial β-hydroxy carbonyl product can react further (in the presence of an acid or a base) to yield an α,β-unsaturated aldehyde or ketone (hereinafter collectively referred to as "α,β-unsaturated carbonyls"). A generic aldol reaction scheme appears as follows:

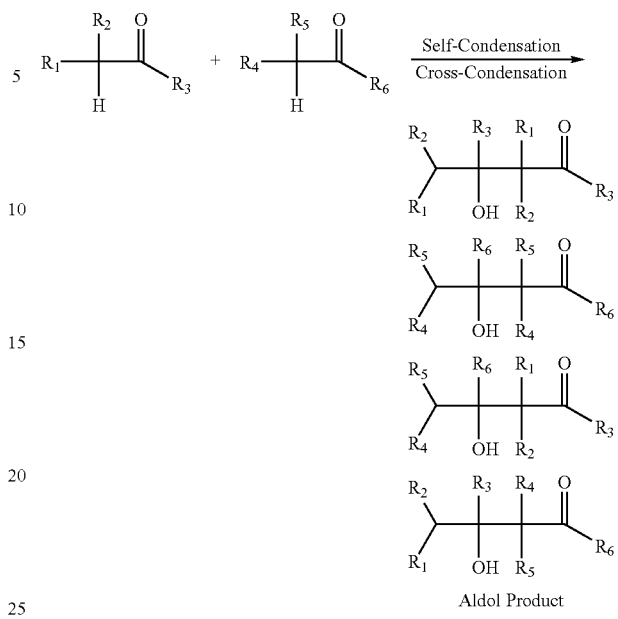

Aldol Product

As shown in this general scheme, $R_1$ through $R_6$ are each independently selected from the group consisting of hydrogen, hydroxy, $C_1$-$C_8$ alkyl, alkenyl, and cycloalkyl, $C_1$-$C_{10}$ mono- and bicyclic aromatic and heterocyclic moieties (including heterocyclic groups derived from biomass), and carbonyls and carbohydrates such as ethanedione, glyceraldehyde, dihydroxyacetone, aldotetroses, aldopentoses, aldohexoses, ketotetroses, ketopentoses, ketohexoses, and the like (without limitation).

However, when one of the carbonyl reactants lacks an alpha-position hydrogen, or cannot form an enolate, or otherwise has a relatively unreactive carbonyl group, the resulting reaction (commonly referred to as a "crossed" aldol reaction) yields a major product, usually in good yield. The mechanism is conventionally considered to be a nucleophilic addition of an enolate ion onto the carbonyl group of another, un-ionized reactant. The aldol reaction is generally quite selective, with yields greater than 80%.

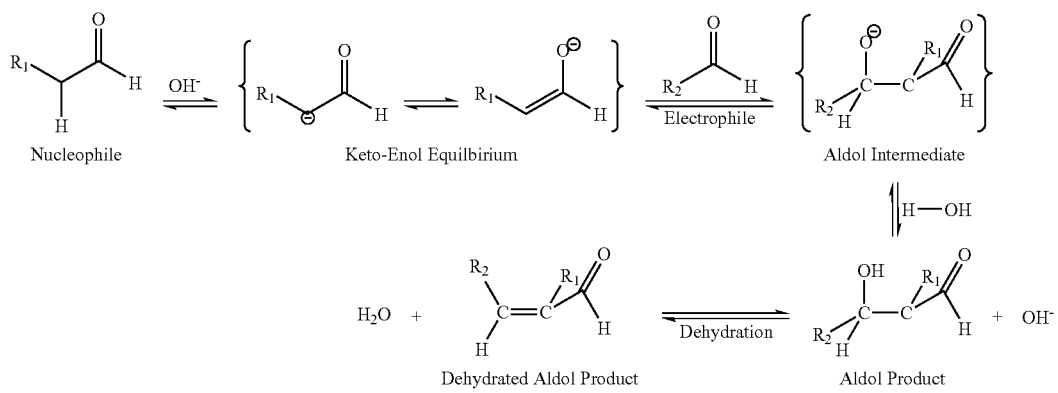

When two different aldehydes or ketones are reacted, and both reactants have an alpha-position hydrogen, four aldol products are possible:

The scientific literature describes a host of variations on the basic aldol condensation mechanism shown above. See, for example, Published U.S. Pat. Appl. 2005/0,004,401; U.S. Pat.

No. 5,583,263; U.S. Pat. No. 5,840,992; U.S. Pat. No. 5,300,654; Kyrides (1933) *J. Amer. Chem. Soc.* 55:3431-3435; and Powell (1924) *J. Amer. Chem. Soc.* 46:2514-17.

Published PCT Appl. WO 00/00456 describes performing aldol condensation reactions using a base-modified clay as a catalyst. The resulting aldols may be reacted further via hydrogenation to yield the corresponding 1,3-diols. Similarly, Published U.S. Patent Appl. 2004/0,138,510 describes co-producing unsaturated aldehydes via a crossed-aldol condensation catalyzed by a water-soluble phase-transfer catalyst. The resulting aldols may be further reacted to yield desired alcohol products or saturated aldehyde feedstocks. Published PCT Appl. WO 01/02330 describes an aldol reaction between an aldehyde and formaldehyde (i.e., a crossed-Cannizzaro reaction), followed by hydrogenation of the aldol product to yield polyols having three or four hydroxyl groups.

Japanese Patent JP 62 192 335 describes a process for making diacetone alcohol. The process includes subjecting acetone to an aldol condensation in the presence of magnesium oxide containing a metallic catalyst selected from sodium, copper, zinc, zirconium, manganese, iron, nickel or chromium.

Aqueous-phase aldol condensation reactions have previously been carried out with glyceraldehyde, dihydroxyacetone, formaldehyde and butyraldehyde using both homogeneous and heterogeneous base catalysts. See Gutsche et al. (1967) *J. Amer. Chem. Soc.* 89:1235, and Serr-Holm et al. (2000) *Appl. Catal. A* 198:207. Cross condensation of furfural with acetone has been conducted using amino-functionalized mesoporous base catalysts, Choudary et al. (1999) *J. Mol. Catal. A* 142:361. Mixed Mg—Al-oxides have previously been used as solid base catalysts for liquid-phase aldol condensation reactions. See Sasaki, Goto, Tajima, Adschiri & Arai (2002) *Green Chem.* 4:285, and Climent, Corma, Iborra, Epping, & Velty (2004) *J. Catal.* 225:316 (2004).

A host of other types of catalytic systems for carrying out aldol and other carbon-carbon bond-forming reactions have been described in the scientific literature. See Serra-Holm et al. (2000) *Applied Catalysis A: General* 198:207-221 (anion exchange resin catalyst); Cordova et al. (2002) *Chem. Commun.* 3024-3025 (cyclic secondary amine catalyst); Aramendia et al. (2004) *J. Mol. Catalysis A: Chemical* 218:81-90 and Aramendia et al. (2004) *Colloids & Surfaces A: Physicochem: Eng. Aspects* 234:17-25 (magnesium- and magnesia-containing catalysts); Climent et al. (2004) J. Catalysis 221: 474-482 (activated hydrotalcite catalyst in a Claisen-Schmidt condensation); and Roelefs et al. (2001) Catalysis Letters 74(1-2):91-94:

In the face of natural disasters (principally hurricanes impacting the gulf coast of the United States) and political instability in the oil-producing countries of the world, the production of liquid fuels from renewable biomass resources is becoming increasingly more attractive. This attractiveness is further heightened as gasoline- and diesel-powered hybrid electric vehicles, having overall energy efficiencies comparable to vehicles powered by fuel cells, are being sold commercially. For example, see Weiss, Heywood, Schafer & Natarajan, "Comparative Assessment of Fuel Cell Cars," No. 001, MIT Laboratory for Energy and the Environment, © 2003. Moreover, many industrialized and industrializing countries, including the United States, grant significant tax incentives for producing liquid bio-diesel for use as transportation fuel. See, for example, U.S. Internal Revenue Service Circular 378, cat. no. 46455F (April 2005).

Approximately 75% of the dry weight of herbaceous and woody biomass is comprised of carbohydrates. See Klass, "Biomass for Renewable Energy, Fuels and Chemicals," Academic Press, San Diego, © 1998. Several processes currently exist to convert carbohydrates to liquid fuels, including forming bio-oils by liquefying or pyrolyzing biomass (Elliott et al. (1991) *Energy and Fuels* 5:399.), producing alkanes or methanol by Fischer-Tropsch synthesis from biomass-derived CO:$H_2$ gas mixtures (Klass, supra), and converting sugars and methanol to aromatic hydrocarbons over zeolites catalysts (see Chen, Degnan & Koenig (1986) *Chemtech* 16:506; and Weisz, Haag & Rodewald (1979) *Science* 206:57).

Currently, however, converting glucose to ethanol is the most widely practiced process for producing liquid fuels from biomass. Katzen & Tsao (2000) *Adv. Biochem. Eng/Biotechnol* 70:77. The overall energy efficiency starting from corn (i.e., the heating value of the product ethanol divided by the energy required to produce ethanol from corn) is about 1.1 without accounting for co-product energy credits. See Shapouri, Duffield & Wang, "The Energy Balance of Corn: An Update," No. 814, U.S. Department of Agriculture, Office of the Chief Economist, © 2002. An astonishing 67% of the energy required to produce ethanol from corn is consumed in the fermentation/distillation process. Of that 67%, over half of the energy is used to distill ethanol from water. See Shapouri et al., supra, and Katzen et al., in "Fuels from Biomass and Wastes," Klass & Emert, Eds., Ann Arbor Science, Ann Arbor, © 1981, pp. 393-402.

In comparison, a practical route to produce long-chain alkanes from an aqueous carbohydrate solution would not require an energy-intensive distillation step because the product long-chain alkanes would spontaneously separate from aqueous solvent. Again using the values provided by Shapouri et al. (supra), it is estimated that the overall energy efficiency for producing alkanes from corn would rise to about 2.2 if the production process did not require a final distillation step. This estimate is underpinned by several well-founded assumptions, namely: (1) that the production process still requires all of the remaining energy needed to produce ethanol from corn; (2) that the yields for sugar and ethanol production are as reported by Klass (supra); and (3) that sugars are converted into alkanes as given by a stoichiometry analogous to Eq. 3, below. (See the Examples for a fully detailed set of calculations.) In short, all other considerations being equal, if the conventional distillation step can be omitted, the overall energy efficiency of producing liquid alkanes from corn can be doubled as compared to conventional techniques requiring fermentation/distillation.

It has recently been shown that an aqueous solution of sorbitol (the sugar-alcohol of glucose) can be converted to hexane (Eq. 1) with a catalyst containing both acid sites (e.g., $SiO_2$—$Al_2O_3$) and metal sites (e.g., Pt or Pd) to catalyze dehydration and hydrogenation reactions, respectively. Huber, Cortright & Dumesic (2004) *Angew. Chem. Int. Ed* 43:1549. Hydrogen for this reaction can be produced from aqueous-phase reforming of sorbitol (Eq. 2) in the same reactor or in a separate reactor with a non-precious metal catalyst. Huber, Shabaker & Dumesic (2003) *Science* 300:2075. The net reaction (Eq. 3) is an exothermic process in which approximately 1.5 moles of sorbitol produce 1 mole of hexane.

$$C_6O_6H_{14} + 6H_2 \rightarrow C_6H_{14} + 6H_2O \qquad (1)$$

$$C_6O_6H_{14} + 6H_2O \rightarrow 6CO_2 + 13H_2 \qquad (2)$$

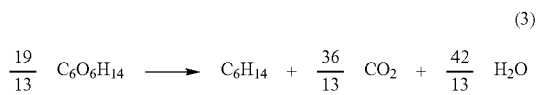

(3)

Alkanes produced in the aqueous-phase dehydration/hydrogenation (APD/H) of carbohydrates could provide a renewable source of transportation fuel to complement the rapidly growing production of bio-diesel from vegetable oils and animal fats. Ma & Hanna (1999) *Bioresour. Technol.* 70:1. Unfortunately, the high volatility of hexane makes it of low value as a fuel additive. Owen & Coley, "Automotive Fuels Handbook," Society of Automotive Engineers, Warrendale, Pa., © 1990. Thus, there remains a long-felt and unmet need for a practical and energy-efficient process for producing high-quality, long-chain liquid fuels (e.g. $C_6$ to $C_{15}$ alkanes) from carbohydrates.

SUMMARY OF THE INVENTION

A first version of the invention is directed to a method for making alkanes. The method comprises subjecting a carbonyl compound in an aqueous reaction solution to at least one self-aldol condensation reaction or a crossed-aldol condensation reaction with another carbonyl compound to yield a beta-hydroxy carbonyl compound and/or an alpha-beta unsaturated carbonyl compound. The beta-hydroxy carbonyl and/or alpha-beta unsaturated compounds are then hydrogenated to yield a saturated polyhydroxy compound. The saturated polyhydroxy compound is then dehydrated and hydrogenated to yield a $C_6$ to $C_{15}$ alkane that is immiscible in the aqueous reaction solution.

It is preferred that the self-aldol condensation reaction or the crossed-aldol condensation reaction is performed in the presence of a catalyst comprising magnesium, zirconium, and oxygen.

Another version of the invention is directed to a method for making alkanes comprising reducing a carbohydrate reactant in an aqueous reaction solution to yield at least one carbonyl compound having an alpha-position hydrogen. The carbonyl compound is then subjected to at least one self-aldol condensation reaction or a crossed-aldol condensation reaction with another carbonyl compound to yield a beta-hydroxy carbonyl compound and/or an alpha-beta unsaturated carbonyl compound. The beta-hydroxy carbonyl and/or the alpha-beta unsaturated carbonyl compounds are then hydrogenated to yield a saturated polyhydroxy compound. Lastly, the saturated polyhydroxy compound is dehydrated and hydrogenated to yield an alkane that is immiscible in the aqueous reaction solution.

The preferred carbohydrate reactant is a sugar or a carbohydrate that is derived from biomass. As noted above, it is preferred that the self-aldol condensation reaction or the crossed-aldol condensation reaction is run in the presence of a catalyst comprising magnesium, zirconium, and oxygen.

Yet another version of the invention is drawn to a method for making alkanes comprising, in an aqueous reaction solution, dehydrating a $C_6$ sugar to yield hydroxymethylfurfural. The hydroxymethylfurfural is then subjected to at least one crossed-aldol condensation reaction with an aldehyde or a ketone to yield a beta-hydroxy carbonyl and/or an alpha-beta unsaturated carbonyl having at least seven (7) carbon atoms. The beta-hydroxy carbonyl and/or alpha-beta unsaturated carbonyl is then hydrogenated to yield a saturated polyhydroxy compound. The saturated polyhydroxy compound is then dehydrated and hydrogenated to yield an alkane having at least seven (7) carbon atoms.

Here, it is preferred that the $C_6$ sugar is derived from biomass. It is also preferred that the crossed-aldol condensation reaction yields a beta-hydroxy carbonyl and/or an alpha-beta unsaturated carbonyl having at least nine (9) carbon atoms, and that the final dehydration and hydrogenation steps yield an alkane having at least nine (9) carbon atoms. It is also preferred that the crossed-aldol condensation reaction yields a beta-hydroxy carbonyl and/or an alpha-beta unsaturated carbonyl having at least eleven (11), at least thirteen (13), or at least fifteen (15) carbon atoms, and that the final dehydration and hydrogenation steps yields an alkane having at least eleven (11), at least thirteen (13) or at least fifteen (15) carbon atoms. Regardless of the size of the product alkane, it is preferred that the self-aldol condensation reaction or the crossed-aldol condensation reaction is carried out in the presence of a catalyst comprising magnesium, zirconium, and oxygen.

Yet another version of the invention is a method for making alkanes comprising, in an aqueous reaction solution, dehydrating a $C_6$ sugar to yield hydroxymethylfurfural. The hydroxymethylfurfural is then hydrogenated to yield hydroxymethyltetrahydrofurfural. The hydroxymethyltetrahydrofurfural is then subjected to a self-aldol condensation reaction to yield a $C_{12}$ beta-hydroxy ketone and/or a $C_{12}$ alpha-beta unsaturated ketone. The $C_{12}$ beta-hydroxy ketone and/or the $C_{12}$ alpha-beta unsaturated ketone is then hydrogenated to yield a saturated polyhydroxy compound. Lastly, the saturated polyhydroxy compound dehydrated and hydrogenated to yield a $C_{12}$ alkane. As in the other versions of the invention, it is preferred that the self-aldol condensation reaction is carried out in the presence of a catalyst comprising magnesium, zirconium, and oxygen.

Still yet another version of the invention is directed to a method for making alkanes comprising, in an aqueous reaction solution, dehydrating a $C_6$ sugar to yield hydroxymethylfurfural. The hydroxymethyltetrahydrofurfural is then subjected to a first crossed-aldol condensation reaction with a first carbonyl compound having an alpha-position hydrogen, and then a second crossed-aldol condensation reaction with a second carbonyl compound lacking an alpha-position hydrogen, to yield a di-(beta-hydroxy)carbonyl and/or a di-(alpha-beta unsaturated) carbonyl having at least ten (10) carbon atoms. The di-(beta-hydroxy) carbonyl and/or the di-(alpha-beta unsaturated) carbonyl is then hydrogenated to yield a saturated polyhydroxy compound. The polyhydroxy compound is then dehydrated and hydrogenated to yield an alkane having at least ten (10) carbon atoms. In this version of the invention, it is preferred that the first carbonyl compound is acetone, and that the second carbonyl compound is hydroxymethylfurfural. As in the other versions of the invention, it is preferred that the first crossed-aldol condensation reaction and the second crossed-aldol reaction are carried out in the presence of a catalyst comprising magnesium, zirconium, and oxygen.

Another version of the invention is directed to a method for making $C_1$ to $C_{15}$ alkanes comprising, in an aqueous reaction solution, subjecting a carbonyl compound to at least one self-aldol condensation reaction or a crossed-aldol condensation reaction with another carbonyl compound to yield a beta-hydroxy carbonyl compound and/or an alpha-beta unsaturated carbonyl compound. The beta-hydroxy carbonyl and/or alpha-beta unsaturated compounds are then hydrogenated to yield a saturated polyhydroxy compound. The saturated polyhydroxy compound is then dehydrated and hydrogenated to yield a $C_1$ to $C_{15}$ alkane. As in the other versions of the invention, it is preferred that the self-aldol condensation reaction or the crossed-aldol condensation reaction be carried out in the presence of a catalyst comprising magnesium, zirconium, and oxygen.

Still another version of the invention is directed to a method for making alkanes comprising, in an aqueous reaction solution, dehydrating a $C_5$ sugar to yield furfural. The furfural is then subjected to at least one crossed-aldol condensation reaction with an aldehyde or a ketone to yield a beta-hydroxy carbonyl and/or an alpha-beta unsaturated carbonyl having at least six (6) carbon atoms. The beta-hydroxy carbonyl and/or alpha-beta unsaturated carbonyl is then hydrogenated to yield a saturated polyhydroxy compound. Lastly, the saturated polyhydroxy compound is dehydrated and hydrogenated to yield an alkane having at least six (6) carbon atoms.

Yet another version of the invention is directed to a method for making alkanes comprising, in an aqueous reaction solution, dehydrating a $C_5$ sugar to yield furfural. The furfural is then subjected to a first crossed-aldol condensation reaction with a first carbonyl compound having an alpha-position hydrogen, and then a second crossed-aldol condensation reaction with a second carbonyl compound lacking an alpha-position hydrogen, to yield a di-(beta-hydroxy) carbonyl and/or a di-(alpha-beta unsaturated) carbonyl having at least eight (8) carbon atoms. The di-(beta-hydroxy) carbonyl and/or the di-(alpha-beta unsaturated) carbonyl is then hydrogenated to yield a saturated polyhydroxy compound. The polyhydroxy compound is then dehydrated and hydrogenated to yield an alkane having at least eight (8) carbon atoms.

Another version of the invention is directed to a method for making alkanes comprising, in an aqueous reaction solution, subjecting tetrahydrofurfural to a self-aldol condensation reaction to yield a $C_{10}$ beta-hydroxy ketone and/or a $C_{10}$ alpha-beta unsaturated ketone. The $C_{10}$ beta-hydroxy ketone and/or the $C_{10}$ alpha-beta unsaturated ketone is then hydrogenated to yield a saturated polyhydroxy compound. The saturated polyhydroxy compound is then dehydrated and hydrogenated to yield a $C_{10}$ alkane.

Yet another version of the invention is drawn to a method for making organic compounds. Here, the method comprises, in an aqueous reaction solution, subjecting a carbonyl compound to at least one self-aldol condensation reaction or a crossed-aldol condensation reaction with another carbonyl compound to yield a beta-hydroxy carbonyl compound and/or an alpha-beta unsaturated carbonyl compound. The beta-hydroxy carbonyl and/or alpha-beta unsaturated compounds are then hydrogenated to yield a polyhydroxy compound. As noted above, the hydrogenation may be complete, so as to yields saturated polyhydroxy compounds. (Likewise, the saturated polyhydroxy compounds may optionally be dehydrated and hydrogenated, as not note earlier, to yield alkanes that are immiscible in the aqueous reaction solution.) Alternatively, polyhydroxy compounds may only be dehydrated (i.e., the final hydrogenation step is omitted) to yield a $C_6$ to $C_{15}$ alkene.

These and other versions of the invention are described in the accompanying detailed description and attached claims.

BRIEF DESCRIPTION OF THE FIGURES

FIGS. 2A, 2B, 2C, and 2D are histograms depicting carbon selectivities from four-phase dehydration/hydrogenation processing of various condensed feeds. FIG. 2A depicts the results of processing furoin; FIG. 2B depicts the results of processing 1:1 and 1:2 mixtures of furfural (Fur) and acetone (Ace); FIG. 2C depicts the results of processing 1:10 and 1:1 mixtures of hydroxymethylfurfural (HMF) and acetone (Ace); FIG. 2D depicts the results of self-condensing (SC) tetrahydrofuran-3-carboxyaldehyde (THF3A) and tetrahydrofuran-2-carboxyaldehyde (THF2A).

FIG. 10A shows the results for furfural:acetone (molar ratio of 1:1) over fresh catalyst at various condensation temperatures followed by hydrogenation at 393 K. FIG. 10B shows the results of HMF:acetone (molar ratio of 1:1) over fresh catalyst at various condensation temperatures followed by hydrogenation at 393 K.

DETAILED DESCRIPTION OF THE INVENTION

Figure 1:
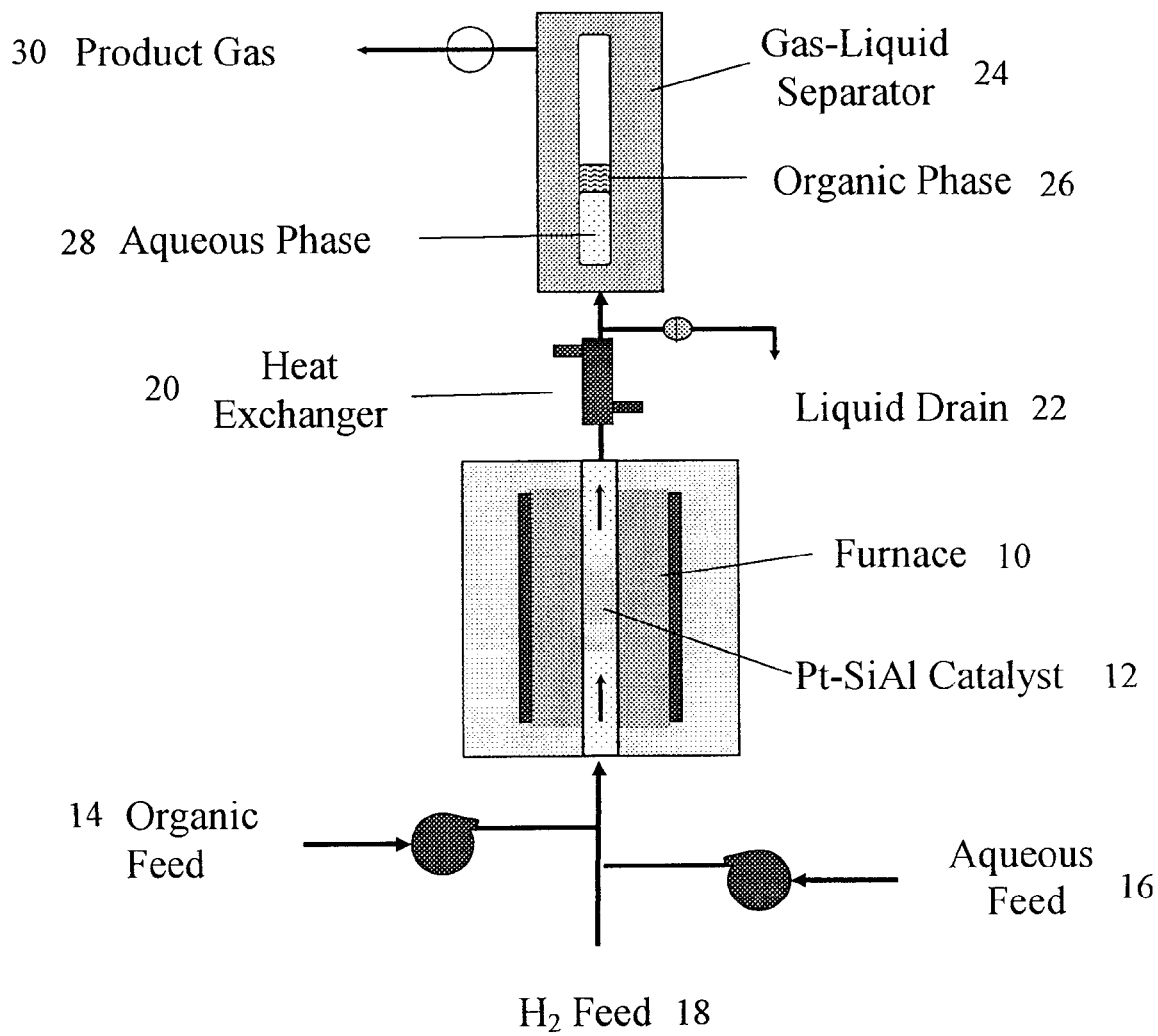
FIG. 1 is a schematic representation of a four-phase dehydration/hydrogenation reactor that can be used to carry out the reactions described herein.

In the present invention, long-chain alkanes are formed by linking carbohydrate-derived moieties via new C—C bonds prior to aqueous phase dehydration/hydrogenation (APD/H) processing. In essence, the chain-length of the carbohydrate feed stocks (preferably derived from biomass) are increased to lengths suitable for long-chain alkanes. The resulting long-chain β-hydroxy carbonyl compounds are then reacted further to reduce the carbonyl groups, either to yield useful feedstocks for making organic chemicals or to yield alkanes, ethers, and the like, suitable for combustion as diesel fuel. The carbon-carbon bonds are created via one or more aldol condensation reactions, preferably using a catalyst comprising a combination of magnesium, zirconium, and oxygen.

Thus, the present invention is directed to a catalytic process for converting carbohydrates in general, and biomass-derived carbohydrates in particular, to liquid, long-chain alkanes in the higher mass ranges (i.e., from $C_6$ to $C_{15}$) that can be used as sulfur-free fuel components. In the complete process, the C—O—C linkages (as found in disaccharides) are broken by acid or enzymatic hydrolysis to form monocarbohydrates. New carbon-carbon bonds are then formed between carbohydrate-derived moieties via a dehydration step (preferably acid catalyzed) coupled with one or more aldol condensation (base catalyzed) steps.

The catalysts used in the aldol reactions, as well as the hydrogenation reactions, are stable, mixed-oxide base catalysts. The preferred catalyst comprises a combination of magnesium, zirconium, and oxygen. Other catalysts, including mixtures of catalysts can be used, including, without limitation: Si—Mg—O, Mg—Ti—O, Y—Mg—O, Y—Zr—O, Ti—Zr—O, Ce—Zr—O, Ce—Mg—O, Ca—Zr—O, La—Zr—O, B—Zr—O, La—Ti—O, B—Ti—O or combinations thereof. If an impregnated catalyst is desired or expedient, various supports, may be used, including, without limitation: $ZrO_2$, $TiO_2$, carbon, carbon nanotubes, nanoporous support, ceria, SiO—AlO, silica nitride, boron nitride, trimethylethoxysilane on $SiO_2$, or mixtures of thereof.

Different atomic ratios of Mg/Zr or the combinations of various other elements constituting the mixed oxide catalyst may be used ranging from about 0.01 to about 50. In case of hydrogenation reactions, metals or alloys of Pd, Pt, Ni, Fe, Cu, Ru, Co, Ir, Rh, with promoters such as Au, Ag, Cr, Zn, Mn, Sn, Bi, Pb may be used in various loadings ranging from about 0.01 to about 20 wt %. The catalysts may be used neat or impregnated on/in a support. The catalysts are preferably made by the sol-gel technique, which allows for control of pH, ageing time, temperature, and drying. Catalysts are preferably calcined at a temperature of from about 200 to about 700° C.

The reactions described herein may be carried out in any reactor of suitable design, including batch and semi-batch reactors, as well as continuous flow reactors, without limitation as to design, size, geometry, flow rates, etc. (e.g., plug-flow reactors, continuous stirred-tank reactors, and the like). Preferred reaction parameters are given below and in the examples. Generally, reaction pressures run from atmospheric to about 100 atm, with temperatures ranging roughly from about 0° C. to about 300° C.

Water is the preferred solvent. Miscible two-part solvent systems comprising water and another water-miscible solvent (such as dimethylformamide, dimethylsulfoxide, 1-methyl-2 pyrrolidinone (NMP), polyvinylpyrrolidone, acetonitrile, polyethylene glycerol, butyl acetate, methanol, acetone, ethanol, etc.) may be also used. Alternatively, a two-component, two-phase solvent system may be used. Here, water is the first solvent, and the second solvent is immiscible in water, such as $CH_2Cl_2$, methyl-isobutyl ketone, toluene, benzene, furan, benzonitrile, etc. Similarly, a three-component, two-phase system comprised of water/solvent 2/solvent 3 may also be used. In this solvent system, both solvent 2 and solvent 3 are immiscible in the water.

In the preferred embodiment, the dehydration/hydrogenation reactions are carried out in four-phase reactor system as shown in FIG. 1. The reactor system comprises: (i) an aqueous inlet stream 16 containing the large water-soluble organic reactant; (ii) a long-chain alkane (e.g., hexadecane) inlet stream 14; (iii) a hydrogen inlet gas stream 18; and (iv) a solid catalyst ($Pt/SiO_2$—$Al_2O_3$) 12 disposed within a furnace 10. See FIG. 1. The reactor also includes a heat exchanger 20, a liquid drain 22, and a gas-liquid separator 24. The product gas is removed from the gas-liquid separator at outlet 30. The organic phase 26 and the aqueous phase 28 separate spontaneously within the gas-liquid separator. As dehydration/hydrogenation takes place, the aqueous organic reactant becomes more hydrophobic, and the long-chain alkane stream (e.g., hexadecane) removes hydrophobic species from the catalyst before they go on further to form coke. In an industrial setting, the alkanes produced from the reaction would be recycled to the reactor and used for the alkane feed.

Reaction kinetics experiments conducted with pure water as the aqueous feed showed that only a small amount of hexadecane was converted to lighter alkanes in the four-phase dehydration/hydrogenation reactor (four-phase D/H reactor) system illustrated in FIG. 1 (0.007 μmol $min^{-1}$ $g_{cat}^{-1}$). (In the Examples that follow, this low reactivity was subtracted from all of subsequent experimental data.)

To benchmark the performance of the four-phase D/H reactor, a test reaction was utilized: a 5 wt % aqueous solution of sorbitol was converted at differing feed rates of the hexadecane alkane stream. Results for these measurements showed that increasing the hexadecane flow rate decreased the conversion of sorbitol (see the Examples at Table 7, entries S1 to S3). Importantly, no major differences were observed in the selectivity of the reaction when the hexadecane-to-water flow rate ratio was increased (see Table 8, entries S1 to S3). Of particular note is that Tables 8 and 9 report data collected from the four-phase D/H reactor at high conversion levels (>70%), where the desired alkanes are the primary product. At these high conversions and slow liquid flow rates, it is possible that transport limitations occur that decrease the reaction rates, perhaps significantly. See Shabaker, Davda, Huber, Cortright & Dumesic (2003) *J. Catal.* 215:344.

By way of an initial experiment, furoin, furfural-acetone (1:1), and furfural-acetone (2:1) were hydrogenated in methanol in a stainless steel batch reactor (Parr Instrument Company, Moline, Ill.) at 55 bar $H_2$ pressure and 393 K, in the presence of a $Pd/Al_2O_3$ catalyst. The furoin was purchased from Aldrich Chemical, Milwaukee, Wis., and prepared from furfural by the Pinnacol coupling reaction, Zhang & Li (1998) *J. Chem. Soc., Perkin Trans.* 1 :3131. The furfural acetone (1:1) was purchased from Aldrich and prepared by aldol condensation of furfural and acetone. The furfural-acetone (2:1) was prepared by aldol condensation of furfural-acetone with furfural and NaOH.) This hydrogenation step was carried out to minimize possible coking reactions that may take place from unsaturated molecules on the $Pt/SiO_2$—$Al_2O_3$ catalyst in the four-phase D/H reactor, and to increase the solubility of the condensed products in water.

The hydrogenated compounds were then dissolved in water and converted to alkanes in the four-phase D/H reactor. The main products of the hydrogenated furoin were n-$C_9$ and $C_{10}$ alkanes. See FIG. 2A, which is a histogram of the results. The Y-axis depicts the carbon selectivity (in percentage); the X-axis depicts alkane chain length (with $CO_2$ being depicted on the far left of the graph).

The hydrogenated furfural-acetone (1:1) was added to both water and hexadecane, and both feeds produced mainly n-$C_7$ and $C_8$ alkanes in the four-phase D/H process (see Table 2, entries 2 and 3). Hydrogenated furfural-acetone (2:1) produced primarily n-$C_{11}$ to $C_{13}$ alkanes from the four-phase D/H reactor. See FIG. 2B, which is a histogram of the results.

Furfural-acetone (1:1) could also be hydrogenated in water without using methanol as a solvent (Tables 1 and 2, entry 4). In this step, the furfural-acetone (1:1) adduct, $Pd/Al_2O_3$ and water were introduced into a Parr reactor, which was subsequently pressurized with $H_2$ (55 bar) and heated to 393 K. As shown in entry 4 of Tables 1 and 2, this reaction yielded an aqueous solution of 12.5 wt % hydrogenated furfural-acetone (1:1), and this feed produced primarily n-$C_7$ and $C_8$ alkanes in the four-phase D/H reactor. The results from these experiments indicate that the present invention for producing liquid alkanes from biomass-derived resources does not require the use of alcohol solvents, and it is not limited to dilute aqueous feeds. (Note that whereas the solubility of furfural-acetone (1:1) is relatively low in water, hydrogenation of the furan ring in the adduct increases the solubility in water to levels higher than 35 wt %.)

Aldol condensation reactions are particularly relevant for producing large organic compounds from biomass because various carbonyl compounds can be formed from carbohydrates, including furfurals, dihydroxyacetone, and acetone. For example, glucose and xylose do not undergo aldol condensation reactions because the carbonyl group undergoes intramolecular reactions to form ring structures. See Collins & Ferrier, "Monosaccharides," Wiley, West Sussex, England, © 1995, and Gutsche et al. (1967), *J. Amer. Chem. Soc.* 89:1235. But dehydrating glucose and xylose (using mineral or solid acid catalysts) yields 5-hydroxymethylfurfural (HMF) and furfural, respectively. See Moreau, Durand, Peyron, Duhamet & Rivalier (1998) *Ind. Crop. Prod.* 7:95; Moreau et al. (1996) *Appl. Catal. A* 145:211; Lourvanij & Rorrer (1993) *Ind. Eng. Chem. Res.* 32:11; and J. Lewkowski (2001) *ARKIVOC* 2001, vol. 17.

Both HMF and furfural have an aldehyde group, and while they cannot undergo self condensation (because they do not have an alpha-position hydrogen atom) they can condense with other molecules that can form carbanion species, such as acetone, dihydroxyacetone or glyceraldehyde. Acetone can be produced from the fermentation of glucose (see Klass, supra), and dihydroxyacetone and glyceraldehyde can be produced from the retro-aldol condensation of glucose. See Kabyemela et al. (1999) *Ind. Eng. Chem. Res.* 38:2888. In the present invention, dehydration, hydrogenation, and aldol condensation reactions are linked to yield long-chain alkanes. See Reaction Schemes 1 and 2:

Reaction Scheme 1

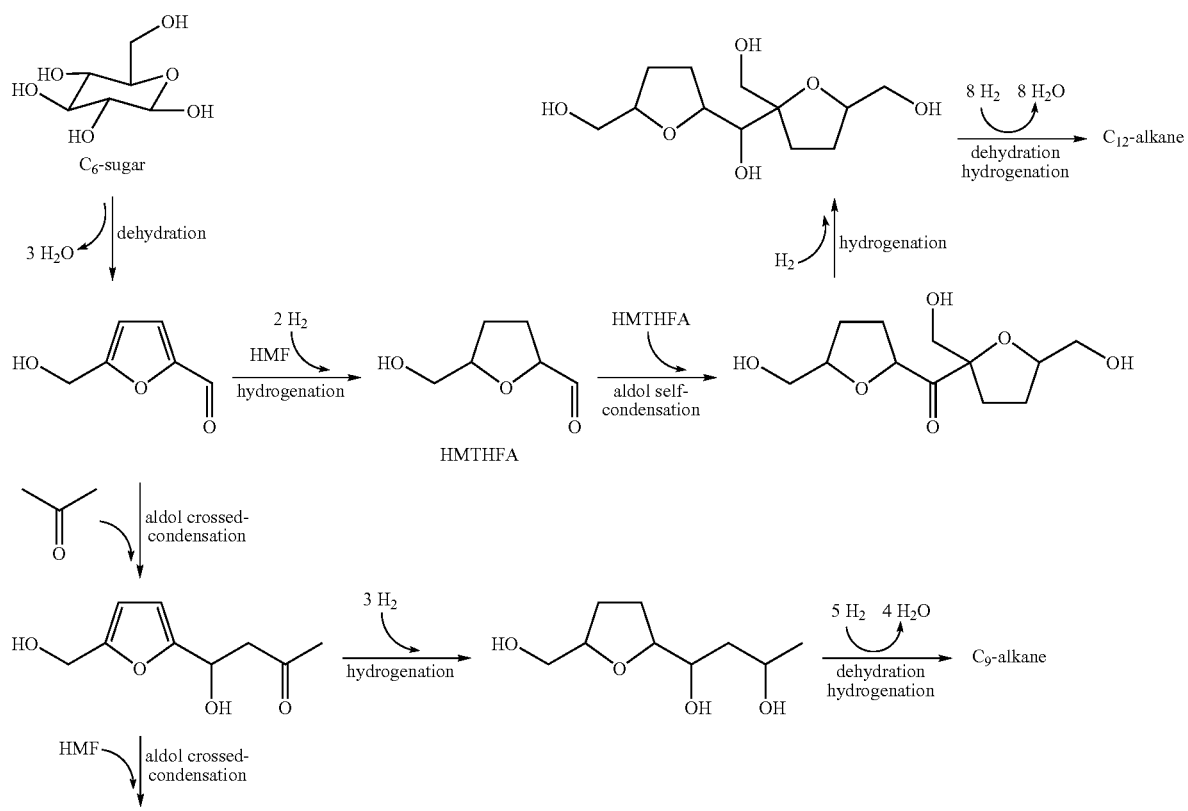

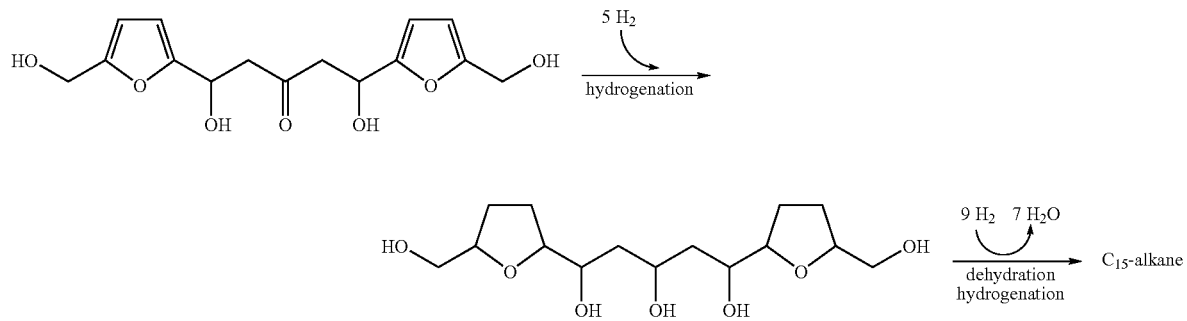

Crossed aldol condensation of HMF with acetone was carried out with HMF:acetone molar ratios of 1:1 and 1:10 using a mixed Mg—Al-oxide catalyst at room temperature (see Tables 1 and 2, entries 6 to 9). The Mg—Al-oxide catalyst was prepared by co-precipitation, similar to the method reported elsewhere. Sasaki, Goto, Tajima, Adschiri & Arai (2002) *Green Chem.* 4:285. Climent, Corma, Iborra, Epping, & Velty (2004) *J. Catal.* 225:316.

The condensed molecules were then hydrogenated in a batch reactor in a methanol/$H_2O$ solvent for the HMF:acetone (1:1)-1 and (1:1)-2 feeds, followed by conversion to alkanes in the four-phase D/H reactor. All other feeds described herein were batch-hydrogenated in $H_2O$. As shown in FIG. 2C, the condensed HMF:acetone feeds produced mainly $C_8$ to $C_{15}$ alkanes in the four-phase D/H reactor, depending on the HMF:acetone ratio used in the aldol condensation step. In FIG. 2C, the solid bars represent the 1-to-10, HMF-to-acetone feed; the unshaded bars represent the 1-to-1, HMF-to-acetone feed. When the HMF:acetone ratio decreases, the alkane distribution shifts to lighter alkanes (see FIG. 2C). The selectivity can also be shifted to heavier alkanes by increasing the extent of conversion for the aldol condensation step of HMF:acetone (see Table 2, entries 6 and 7).

Reaction Scheme 2

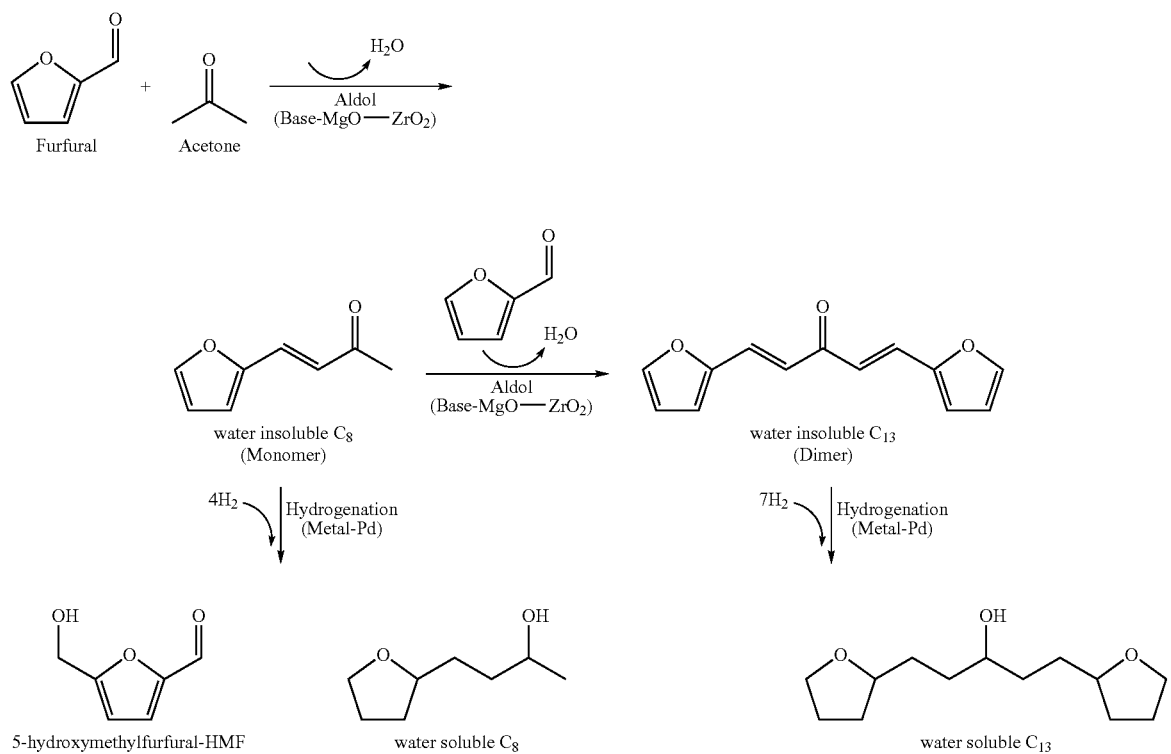

Reaction Scheme 2 shows the corresponding set of reactions wherein furfural and acetone are the reactants for the initial aldol condensation reaction (rather than hydroxymethylfurfural or hydroxymethyltetrahydrofurfural, as shown in Reaction Scheme 1).

TABLE 1

Values for conversion and process conditions for four-phase dehydration/hydrogenation (D/H) of biomass-derived molecules. (See the Examples for full experimental details.) All four-phase D/H reactions were carried out at 523 to 538 K, 52 to 60 bar and $H_2$ gas hourly space velocity (v/v) of 1000 to 3000 $h^{-1}$. A 4 wt % $Pt/SiO_2$—$Al_2O_3$ catalyst was used for these reactions. Each experimental point was collected after 20 h time-on-stream. Condensed feeds were prepared by aldol condensation at room temperature using Mg—Al-oxide and NaOH catalyst. Feed key: SC = self condensed; Fur = furfural; Ace = acetone; HMF = 5-hydroxymethylfurfural; THF3A = tetrahydrofuran-3 carboxyaldehyde; THF2A = tetrahydrofuran-2 carboxyaldehyde. Numbers listed in parantheses indicate molar ration of feeds. All feeds were hydrogenated in a Parr reactor with $Pd/Al_2O_3$ catalyst prior to conversion in the four-phase D/H reactor. Entries 1 to 3 and 5 to 7 were hydrogenated in methanol or a methanol/water mixture, with all other feeds being hydrogenated in $H_2O$. Abbreviations: Wt (%) refers to weight percent organics in aqueous feed solution. WHSV is weight hourly space velocity; mass of aqueous feed solution per mass of catalyst per hour. Org/Aq is the organic (hexadecane)-to-aqueous volumetric feed ratio.

| Entry | Feed | Wt (%) | WHSV ($h^{-1}$) | Org/Aq | % Carbon in Phase Org | Gas | Aq |
|---|---|---|---|---|---|---|---|
| 1 | Furoin | 2.0 | 0.26 | 3.0 | 69.2 | 18.5 | 2.3 |
| 2 | Fur:Ace (1:1)-1 | 1.9 | 0.26 | 3.0 | 100.0 | 6.3 | 1.6 |
| 3 | Fur:Ace (1:1) org* | 5.0 | 0.51 | ∞ | 73.2 | 7.8 | NA |
| 4 | Fur:Ace (1:1)-3 | 12.5 | 0.29 | 3.0 | 91.2 | 4.1 | 0.7 |
| 5 | Fur:Ace (2:1) | 1.0 | 0.29 | 3.0 | 79.0 | 2.4 | 0.8 |
| 6 | HMF:Ace (1:1)-1 | 1.8 | 0.25 | 3.0 | 66.1 | 15.7 | 1.5 |
| 7 | HMF:Ace (1:1)-2† | 1.9 | 0.26 | 3.0 | 69.5 | 7.7 | 0.9 |
| 8 | HMF:Ace (1:1)-3 | 1.8 | 0.29 | 3.0 | 53.3 | 31.1 | 2.3 |
| 9 | HMF:Ace (1:10) | 9.5 | 0.35 | 0.7 | 77.2 | 10.3 | 20.0 |
| 10 | HMF:Fur:Ace (1:1:2) | 1.9 | 0.29 | 3.0 | 48.5 | 27.8 | 3.1 |
| 11 | SC THF3A | 5.0 | 0.35 | 0.7 | 53.2 | 44.1 | 4.2 |
| 12 | SC THF2A | 3.9 | 0.35 | 0.7 | 47.9 | 20.8 | 13.0 |

*Fur:Ace (1:1) org was added to the hexadecane feed and no aqueous flow was used for this feed.
†This feed was condensed with twice the amount of Mg—Al-oxide than the feed above it (Entry 6).

TABLE 2

Selected values for alkane and CO2 selectivities from four-phase dehydration/hydrogenation of biomass derived-molecules. (See the Examples for complete experimental details.) Table 1 contains relevant process conditions, feed key and conversion data. Selectivity = (moles product × number of carbon atoms in product)/(total moles of carbon atoms in products) × 100. The selectivity only takes into account the products in the organic and gas phases. Alkane products are mostly straight chain, except for the SC THF3A and SC THF2A feeds. At lower conversions small amounts of alcohols (<10% of total products) are also observed in the organic phase.

| Entry | Feed | Alkane and $CO_2$ Selectivities (%) | | | | | | | | | | | | | | |
|---|---|---|---|---|---|---|---|---|---|---|---|---|---|---|---|---|
| | | $CO_2$ | $C_1$ | $C_2$ | $C_3$ | $C_4$ | $C_5$ | $C_6$ | $C_7$ | $C_8$ | $C_9$ | $C_{10}$ | $C_{11}$ | $C_{12}$ | $C_{13}$ | $C_{14}$ | $C_{15}$ |
| 1 | Furoin | 5.2 | 5.2 | 0.0 | 2.8 | 8.0 | 9.2 | 1.8 | 0.3 | 5.4 | 26.2 | 34.0 | 0.7 | 0.3 | 0.3 | 0.4 | 0.2 |
| 2 | Fur:Ace (1:1)-1 | 1.8 | 2.2 | 0.0 | 0.0 | 0.1 | 0.2 | 0.3 | 15.0 | 77.7 | 0.6 | 0.2 | 0.4 | 0.3 | 0.4 | 0.4 | 0.4 |
| 3 | Fur:Ace (1:1) org | 0.0 | 4.7 | 0.2 | 1.7 | 1.8 | 2.0 | 1.9 | 4.5 | 71.4 | 2.4 | 2.2 | 2.2 | 2.1 | 2.4 | 0.6 | 0.0 |
| 4 | Fur:Ace (1:1)-3 | 1.7 | 0.4 | 0.0 | 0.1 | 0.1 | 0.1 | 0.2 | 17.1 | 64.4 | 7.4 | 5.8 | 2.5 | 0.1 | 0.1 | 0.1 | 0.0 |
| 5 | Fur:Ace (2:1) | 0.0 | 3.0 | 0.0 | 0.0 | 0.0 | 0.4 | 0.7 | 1.0 | 2.1 | 0.8 | 0.5 | 2.1 | 19.7 | 68.6 | 0.6 | 0.5 |
| 6 | HMF:Ace (1:1)-1* | 6.8 | 3.3 | 0.0 | 0.0 | 6.0 | 14.6 | 9.3 | 0.4 | 6.8 | 9.5 | 0.0 | 0.0 | 0.7 | 8.5 | 19.5 | 14.5 |
| 7 | HMF:Ace (1:1)-2* | 5.0 | 4.0 | 0.0 | 0.0 | 1.5 | 3.2 | 2.2 | 0.4 | 2.9 | 4.6 | 0.2 | 0.4 | 1.5 | 13.5 | 32.9 | 27.6 |
| 8 | HMF:Ace (1:1)-3 | 5.7 | 3.5 | 0.0 | 23.5 | 3.8 | 10.0 | 7.0 | 0.7 | 5.9 | 6.9 | 0.1 | 0.3 | 1.0 | 6.2 | 14.5 | 10.9 |
| 9 | HMF:Ace (1:10)† | 6.0 | 0.9 | 0.0 | 0.0 | 2.6 | 4.8 | 1.1 | 3.9 | 27.4 | 41.2 | 1.9 | 0.2 | 0.5 | 5.1 | 3.6 | 0.8 |
| 10 | HMF:Fur:Ace (1:1:2) | 4.0 | 3.0 | 0.0 | 25.3 | 3.8 | 7.2 | 3.3 | 2.5 | 10.2 | 5.6 | 0.0 | 1.0 | 4.8 | 14.3 | 10.8 | 4.4 |
| 11 | SC THF3A‡ | 9.4 | 0.7 | 0.0 | 4.2 | 23.4 | 25.1 | 0.1 | 3.4 | 6.7 | 11.6 | 14.3 | 0.1 | 0.9 | 0.0 | 0.0 | 0.0 |
| 12 | SC THF2A§ | 11.4 | 1.3 | 0.0 | 5.1 | 15.1 | 9.9 | 0.5 | 5.2 | 13.0 | 17.7 | 19.4 | 0.3 | 0.9 | 0.3 | 0.0 | 0.0 |

*$C_3$ selectivity is zero because acetone was removed during separation of hydrogenated products from methanol-water solution.
†Propane is not included in the alkane selectivity calculation for this feed.
‡Liquid alkanes produced in this feed were mostly branched. The $C_{10}$ alkane was 3-methyl-5-dimethyl-heptane.
§Liquid alkanes produced in this feed were mostly branched. The $C_{10}$ alkane was 4-methylnonane.

To improve the potential practical utility of the invention, it was determined whether hydrogenation of the HMF:acetone adduct could be accomplished without using methanol as a solvent. In this instance, the aldol condensation of HMF:acetone (1:1) was carried out in water over the Mg—Al-oxide catalyst, and Pd/Al$_2$O$_3$ was added to the reaction slurry, followed by treatment with H$_2$ (55 bar) at 393 K in the Parr reactor. Similar to hydrogenation of furfural:acetone in water, it was discovered that hydrogenation of the HMF:acetone adduct increases its solubility in water, and the aqueous solution from this hydrogenation step produced significant amounts of C$_{14}$ and C$_{15}$ alkanes from the four-phase D/H reactor (Table 2, entry 8).

The results shown in Tables 1 and 2 also show that mixtures of HMF and furfural (Table 1 and 2, entry 10) can be condensed with acetone to form alkanes ranging from C$_7$ to C$_{15}$. Unlike producing ethanol by fermentation, in the present invention cellulose and hemicellulose need not be separated to produce liquid alkanes by four-phase D/H processing.

Results for crossed aldol condensation of furfural and HMF with dihydroxyacetone and glyceraldehyde are summarized in entries S15 to S20 of Tables 8 and 9 (see the Examples). These condensation reactions over Mg—Al-oxide catalyst showed a large disappearance of furfural and HMF based on high-performance liquid chromatography ("HPLC") (Table 5); however, as shown in Table 8 less than 30% of the alkane products are heavier than the C$_5$ and C$_6$ reactants (for reactions of furfural and HMF, respectively). Condensing furfural with hydroxyacetone gave an alkane distribution similar to that produced from condensation of furfural with dihydroxyacetone (see Table 8, entry S18). Thus, while making heavier liquid alkanes by crossed aldol condensation of furfural and HMF with dihydroxyacetone, hydroxyacetone, or glyceraldehydes is within the scope of the present invention, the selectivities of these processes makes them less preferred embodiments.

Another route to make large water-soluble organic compounds is to hydrogenate the C=C bonds of HMF and furfural selectively, thereby producing 5-hydroxymethyl-tetrahydrofurfural (HMTHFA) and tetrahydrofuran-2 carboxyaldehyde (THF2A), respectively. These species can form carbanion species and undergo self aldol condensation reactions (see Reaction Scheme 1). The results, tabulated in FIG. 2D (again, Y-axis shows selectivity in percent; X-axis shows chain length in carbon atoms), show that self aldol condensation of tetrahydrofuran-3 carboxyaldehyde and THF2A produced liquid hydrocarbons ranging from C$_8$-C$_{10}$ from the four-phase D/H reactor. THF2A was produced by dehydrogenation of tetrahydrofurfuryl alcohol in the gas phase over a Cu/SiO$_2$ catalyst.

Of particular note is that the conversion of carbohydrates to liquid alkanes involves the storage of a considerable amount of hydrogen in the fuel. In short, essentially one (1) molecule of H$_2$ is used to convert each carbon atom in the carbohydrate reactant to an alkane moiety. The liquid alkanes retain about 90% of the energy content of the carbohydrate and H$_2$ reactants. Thus, the carbon in the carbohydrates serves as an effective energy carrier for transportation vehicles, analogous to the role of carbohydrates as energy storage compounds for living organisms.

The experiments presented to this point demonstrate that liquid alkanes can be produced from biomass-derived compounds, without an expensive distillation step. However, the catalysts used in the initial work were not as robust as desired. Thus, investigations were undertaken to find an effective, robust, and recyclable catalyst that exhibits long-term stability under the aqueous-phase reaction conditions used. After much work, it was found that a catalyst comprised of magnesium, zirconium, and oxygen was the preferred catalyst for use in the present invention.

The preferred catalyst was prepared and characterized as described in the Examples. The preferred atomic ratio of Mg/Zr is about 11.6, although it can vary in the range from about 0.5 to about 50.

Figure 3:
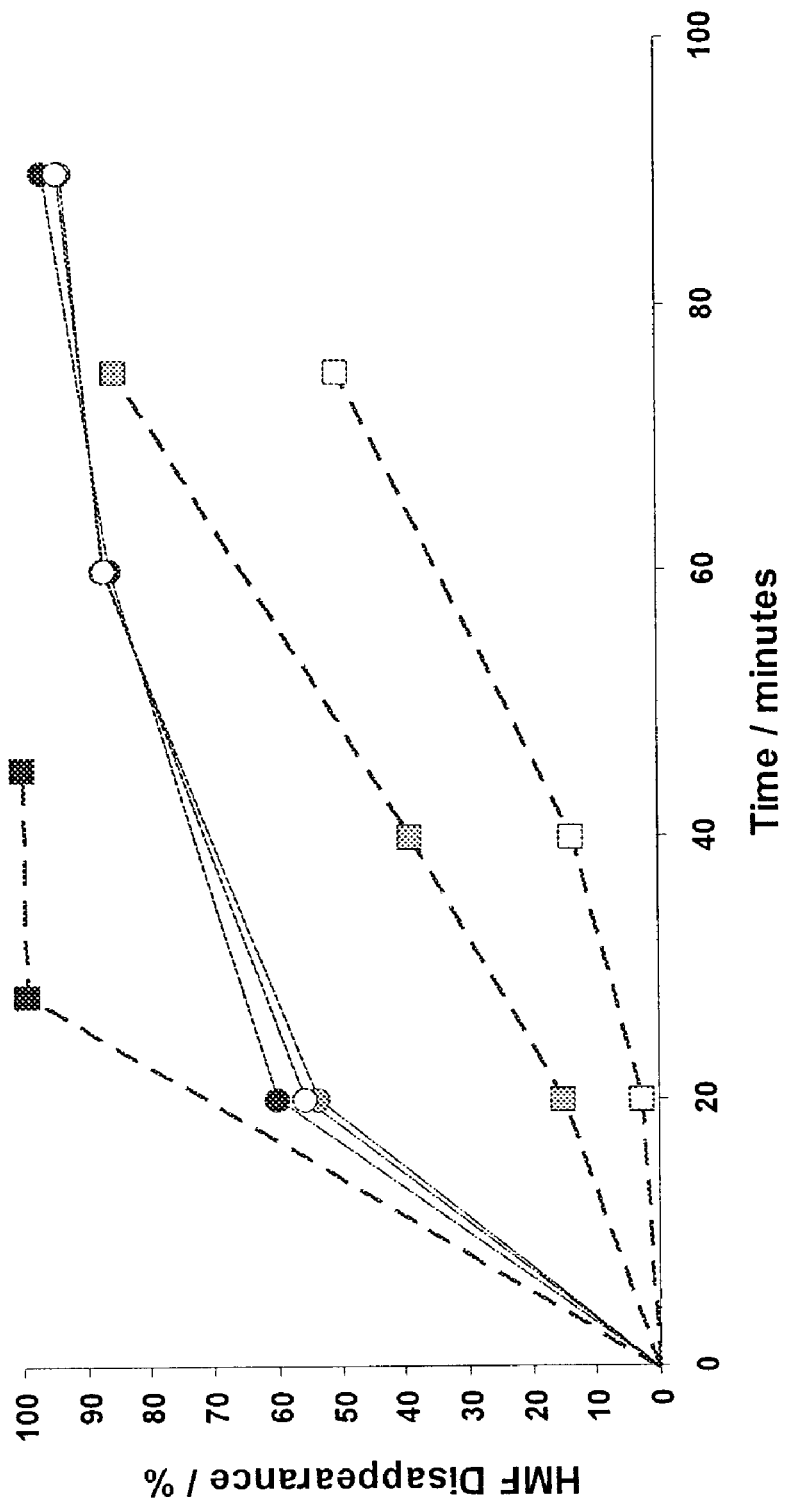
FIG. 3 is a graph depicting the disappearance of HMF versus time in triplicate runs of an HMF/acetone aldol condensation reaction using a mixed Mg—Al-oxide catalyst and the preferred MgO—$ZrO_2$ catalyst. Mixed Mg—Al-oxide: run 1 (black squares), run 2 (grey squares), run 3 (white squares); MgO—$ZrO_2$: run 1 (black circles); run 2 (grey circles), run 3 (white circles). Mixed Mg—Al-oxide runs were carried out at room temperature and pressure, while MgO—$ZrO_2$ runs were carried out at 323 K and atmospheric pressure. HMF:acetone molar ratio was equal to 1:10; 11.2 wt % organics in the aqueous phase. The organic/catalyst mass ratio was 6.

The preferred MgZrO catalyst is remarkably stable, as demonstrated in FIG. 3. FIG. 3 is a graph depicting the disappearance of HMF in triplicate runs of an HMF/acetone aldol condensation reaction as shown in Reaction Scheme 1. Specifically, FIG. 3 is a graph comparing HMF disappearance versus time during an aldol condensation with acetone over a fresh, calcined, recycled mixed Mg—Al-oxide catalyst and the preferred MgO—ZrO$_2$ catalyst. The mixed Mg—Al-oxide catalyzed reactions are depicted in FIG. 3 as follows: run 1 (black squares), run 2 (grey squares), run 3 (white squares). The preferred MgO—ZrO$_2$ catalyzed reactions are depicted in FIG. 3 as follows: run 1 (black circles); run 2 (grey circles), run 3 (white circles). The mixed Mg—Al-oxide runs were carried out at room temperature and pressure, while MgO—ZrO$_2$ runs were carried out at 323 K and atmospheric pressure. HMF:acetone molar ratio was equal to 1:10, with 11.2 wt % organics in the aqueous phase, and an organic/catalyst mass ratio equal to 6. As can be seen in FIG. 3, while the mixed Mg—Al-oxide catalyst displayed highly desirable results in the first run, it displayed markedly diminished catalytic activity in each of runs 2 and 3, respectively. In contrast, the preferred MgO—ZrO$_2$ catalyst displayed consistently high (and essentially unchanged) catalytic activity through all three runs.

Figure 4:
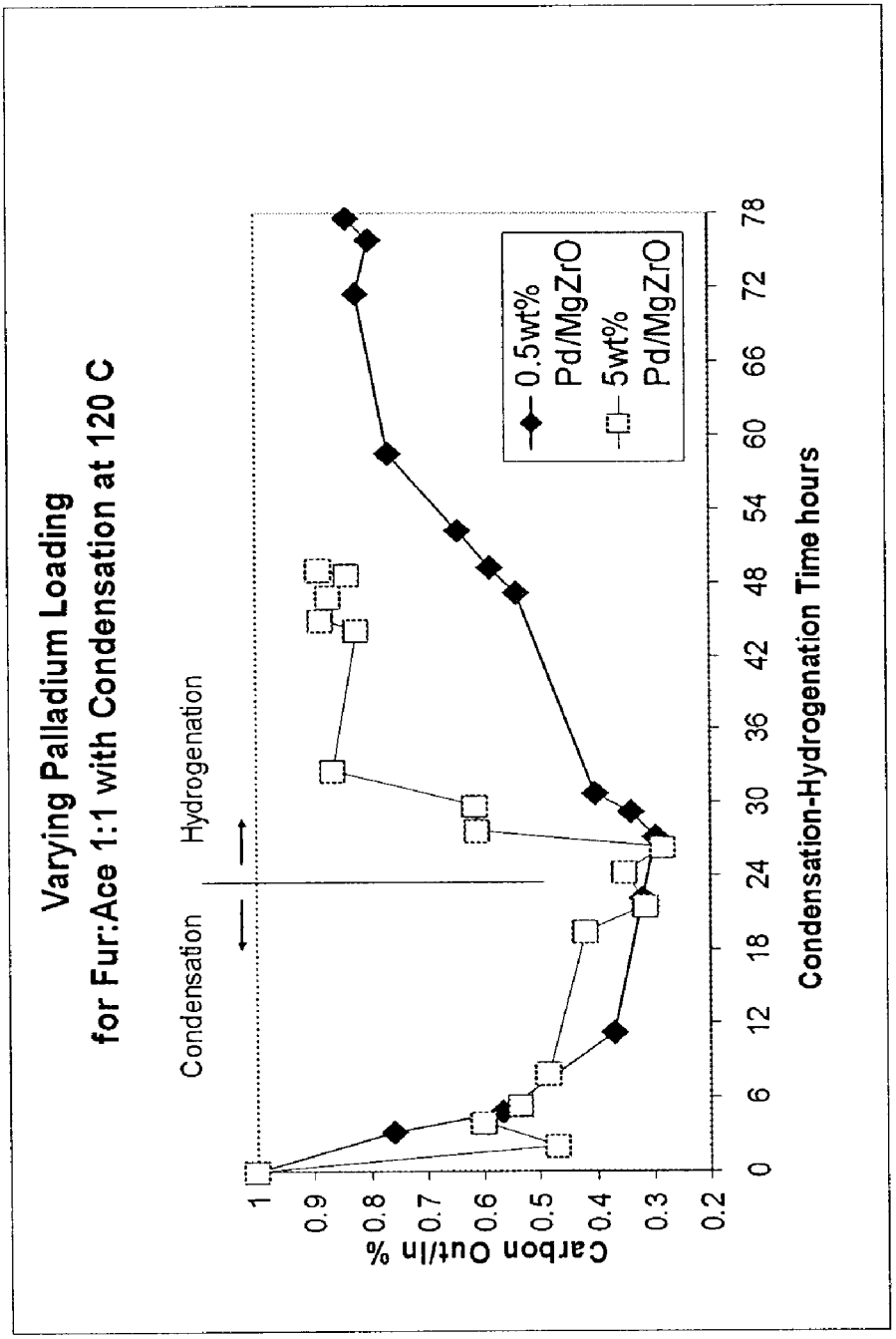
FIG. 4 is a graph depicting the effects of varying the palladium loading on the product mix in a 1-to-1 aldol condensation of furfural and acetone at 120° C.

Adding a noble metal, such as palladium, to the MgZrO catalyst also has a marked impact on the extent of hydrogenation, as shown in FIG. 4. Here, furfural and acetone were subjected to an aldol condensation followed by hydrogenation over a Pd/MgZrO catalyst. The solid diamonds mark a loading of 0.5 wt % palladium/MgZrO, while the open squares mark a loading of 5wt % palladium/MgZrO. Percent yield is shown on the Y-axis; time in hours is shown on the X-axis. This graph clearly shows that the extent of reaction can be controlled by modifying the loading of the catalyst.

Figure 5:
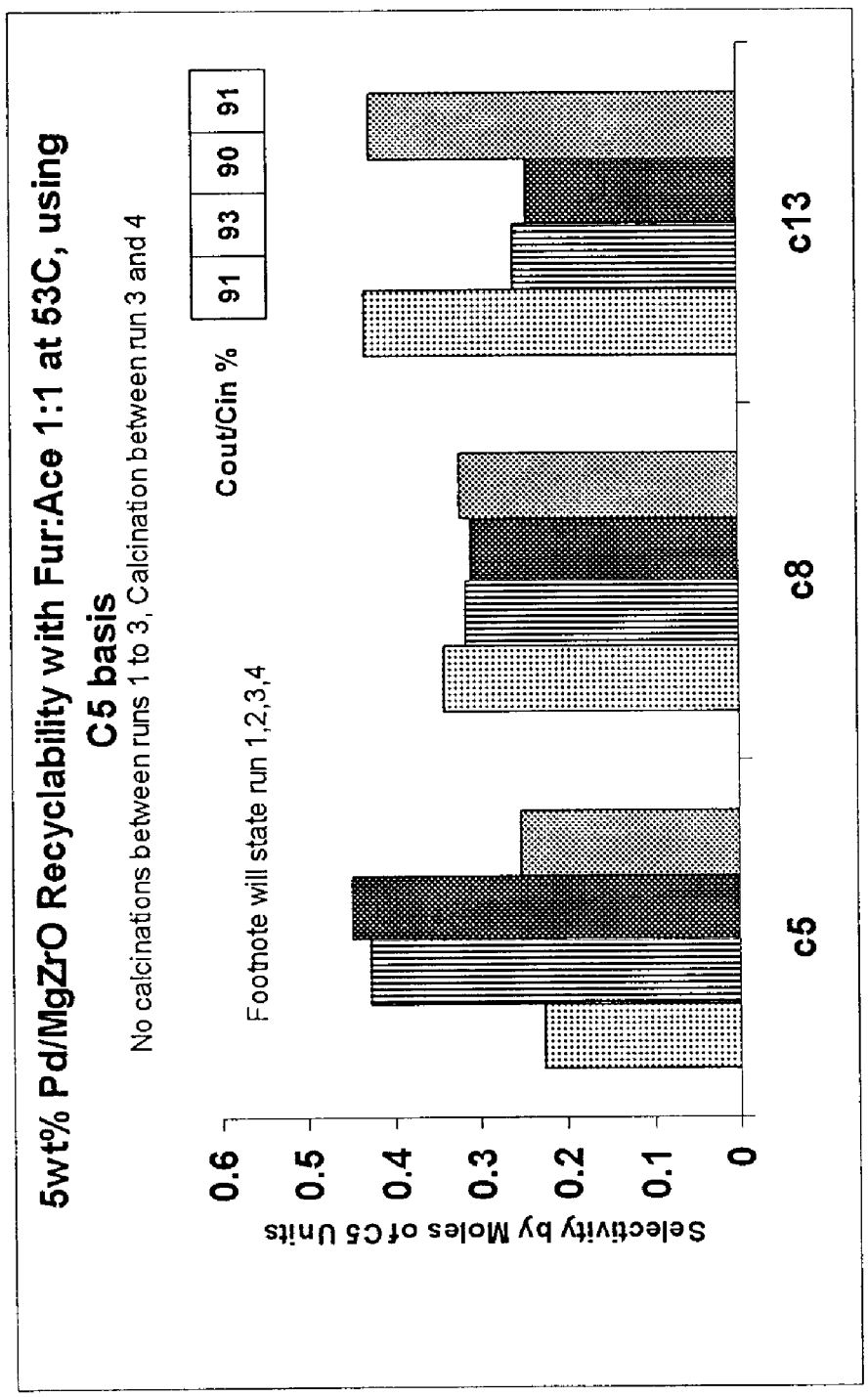
FIG. 5 is histogram depicting the recyclability of the preferred MgZrO catalyst by calcining the catalyst after three identical reaction runs. The histogram depicts selectivity based on $C_5$ (furfural:acetone) units in the aqueous phase after aldol condensation followed by hydrogenation over 5 wt % Pd/MgO—$ZrO_2$ catalyst. (See the examples for how selectivity and overall carbon yield are defined.) Furfural:acetone (molar ratio of 1:1) over fresh and recycled catalyst. 5 wt % organics in the aqueous phase; 326 K and 10 bar He for condensation; 393 K and 55 bar $H_2$ for hydrogenation; organic/catalyst mass ratio of 6, except for run 4 which had a ratio of 9. Key (moving left-to-right in each group of bars: fresh catalyst with calcination ($1^{st}$ bar); first recycle without calcination ($2^{nd}$ bar); second recycle without calcination ($3^{rd}$ bar); third recycle with calcination ($4^{th}$ bar).

Likewise, the ability of the preferred MgZrO catalyst to be regenerated, via calcination, is shown in FIG. 5. Here, a furfural/acetone condensation/hydrogenation reaction was performed, as described earlier. The reaction was run three times in succession, without any calcination of the catalyst. As can be seen from FIG. 5, the relative proportion of C$_5$ alkanes steadily increased from run 1 to run 3. At the same time, the relative proportion of the desired long-chain C$_8$ and C$_{13}$ alkanes gradually decreased from run 1 to run 3. After run 3, the catalyst was calcined, and the reaction was repeated a fourth time. Note that in the fourth run, the catalytic activity returns essentially to the same point as in the first run. This graph shows that the preferred catalyst can be recycled, thereby making the process more economically feasible.

Figure 6:
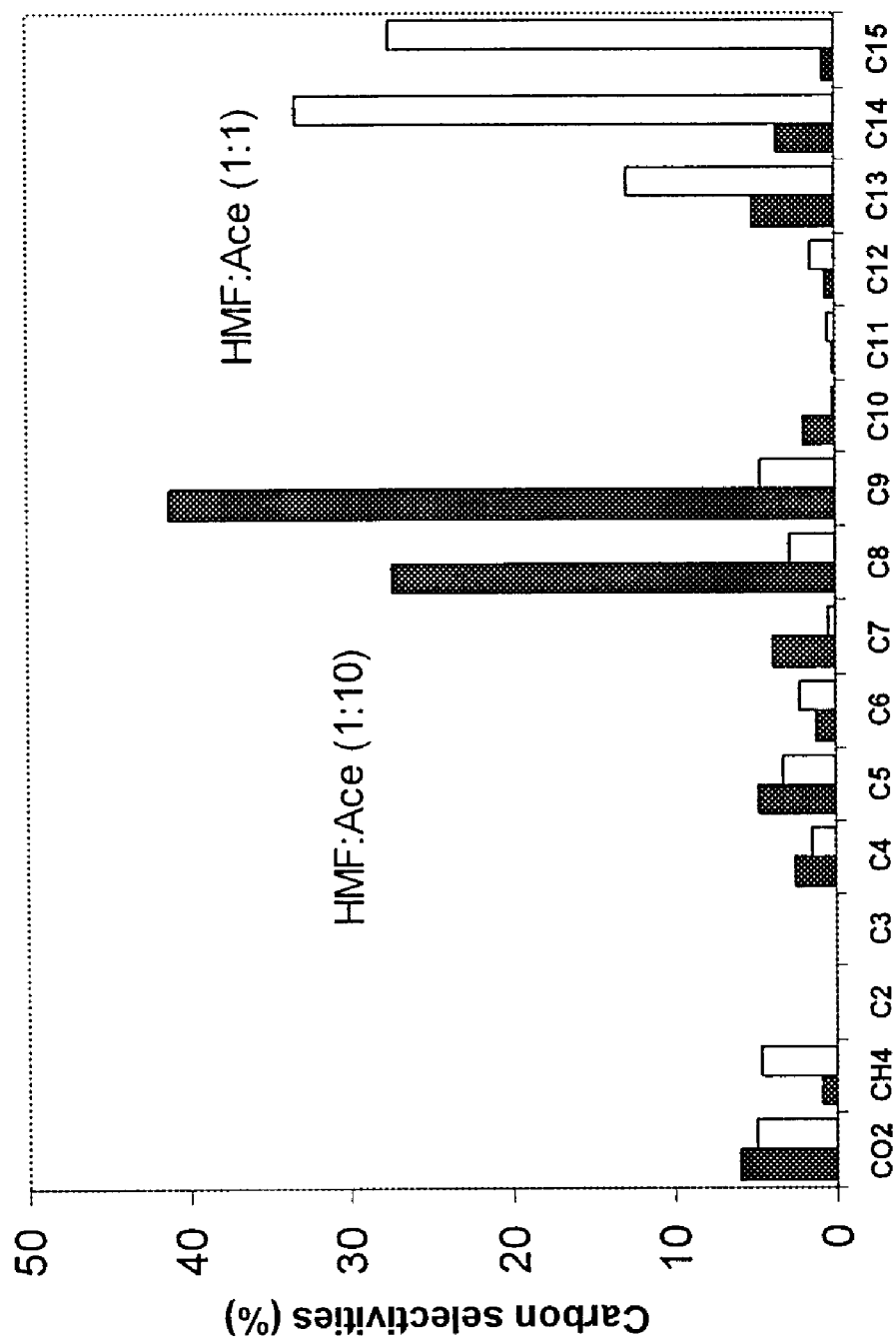
FIG. 6 is a histogram depicting the product mix as a function of feedstock ratio in an aldol cross-condensation reaction between hydroxymethylfurfural and acetone.

As in the reactions described previously, the product mixture using the MgZrO catalyst can be altered by judiciously controlling the feed stock ratios, as shown in FIG. 6. FIG. 6 is a histogram analogous to FIG. 2C. The reaction is a cross-condensation reaction of HMF and acetone, under the same conditions as described for FIG. 2C, with the exception that the MgZrO catalyst was used. Using a feedstock of 1:10, HMF:acetone (solid bars), C$_8$ and C$_9$ alkanes dominate the product mix. Using a feedstock of 1:1 (empty bars), HMF:acetone, C$_{13}$ to C$_{15}$ alkanes dominate the product mix.

Figure 7:
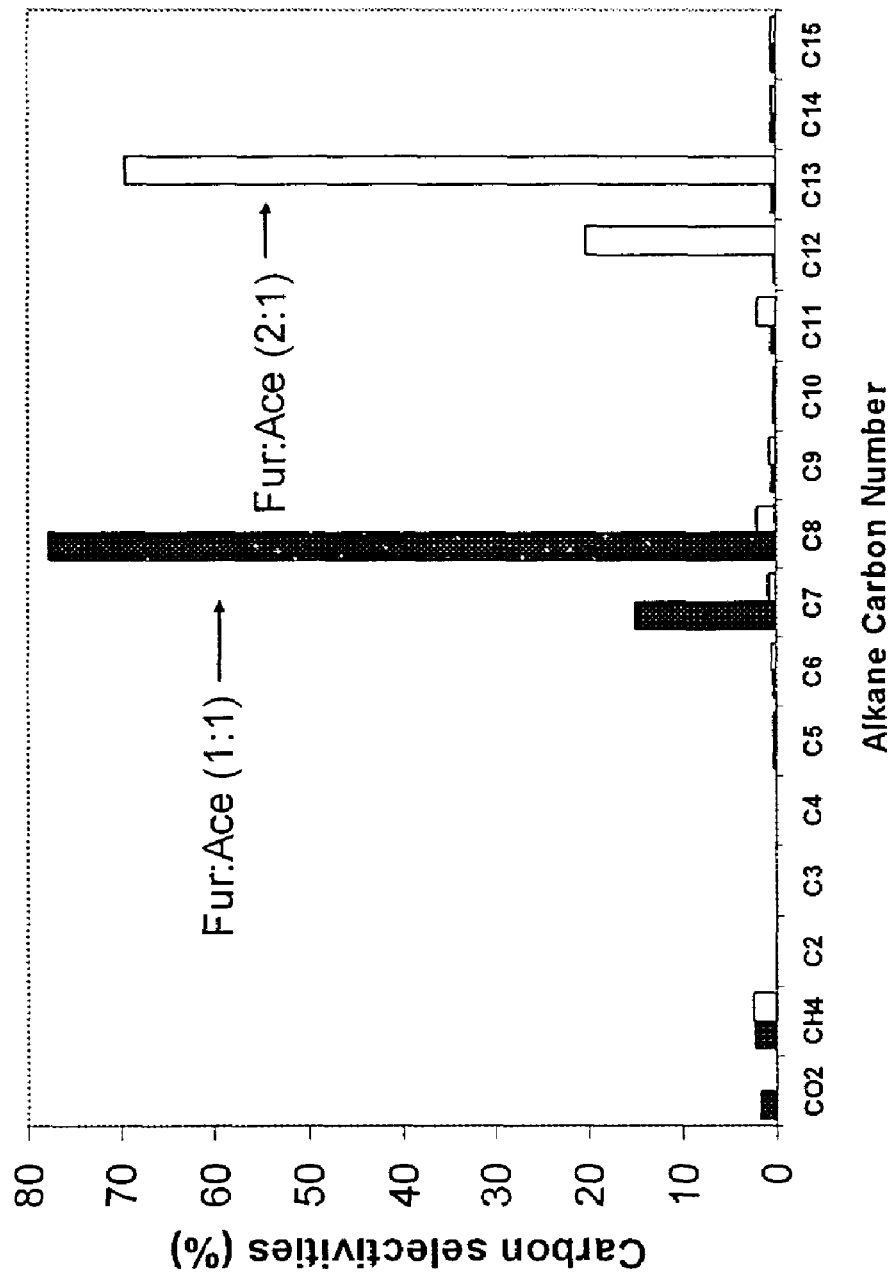
FIG. 7 is a histogram depicting the product mix as a function of feedstock ratio in an aldol cross-condensation reaction 12.5 wt % solution of furfural and acetone.

Similar results are shown when a 12.5 wt % solution of furfural and acetone is used as the feedstock. Using a feedstock of 1:1, furfural:acetone (solid bars), $C_7$ and $C_8$ alkanes dominate the product mix. Using a feedstock of 2:1, furfural:acetone (empty bars), $C_{12}$ and $C_{13}$ alkanes dominate the product mix. Of very considerable note in FIG. 7 is that a mixture of HMF and acetone can be condensed to yield $C_7$ to $C_{15}$ alkanes, indicating that separating cellulose from hemicellulose is not required in the present invention.

Based on these results, an overall organic feed concentration of up to about 50 wt % can be processed according to the present invention. Where cross-condensation reactions are performed, the molar ratio of the cross-condensing species preferably ranges from about 0.001 to about 30.

Figure 8:
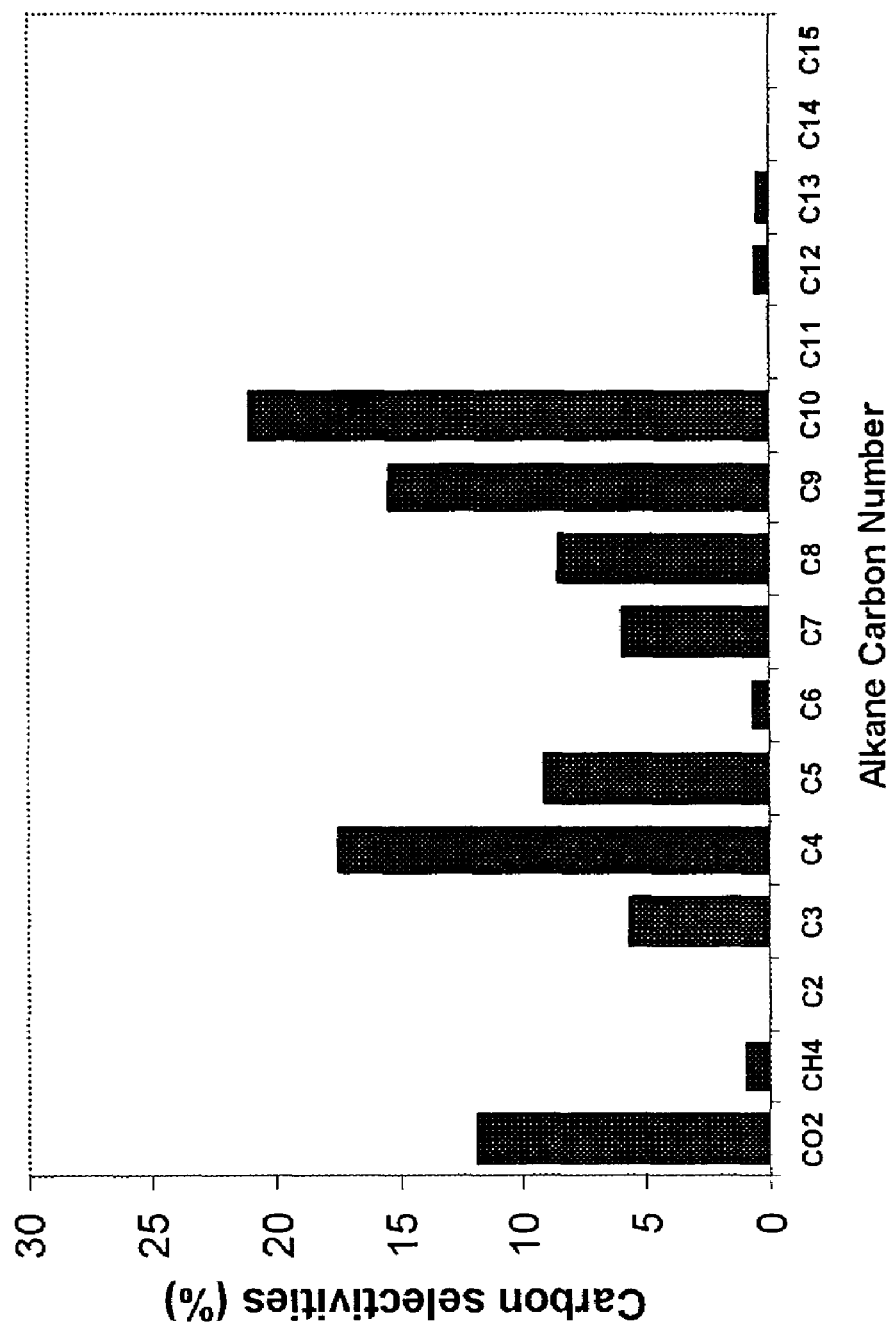
FIG. 8 is a histogram depicting the product mix in an aldol self-condensation reaction tetrahydrofurfural.

Self-condensation of tetrahydrofurfural (under the same conditions noted above) yielded a 55% percent selectivity for producing $C_7$ to $C_{10}$ alkanes, as shown in FIG. 8.

EXAMPLES

Catalyst Preparation and Characterization: Supported Pd and Pt catalysts were prepared by incipient wetness impregnation of $Al_2O_3$ ("Catapal B"-brand, Sasol, Houston, Tex.) and $SiO_2$—$Al_2O_3$ (MS-25-brand, $Al_2O_3$ content 25 wt %, Grace Davison, Columbia, Md.), using tetra-amine platinum (IV) nitrate (Strem Chemicals, Newburyport, Mass.) and tetra-amine palladium (II) nitrate (Strem Chemicals) as the precursor salts. Following impregnation, catalysts were dried in air at 393 K for 12 h and then calcined in a flowing 20% $O_2$/He gas mixture (GHSV ~1000 $h^{-1}$) to 533 K (at 1.3 K/min) and held at this temperature for 2 h. Prior to collecting reaction kinetics data and CO chemisorption measurements, each catalyst was reduced in flowing $H_2$ (GHSV ~250-1000 $h^{-1}$) at a temperature of 723 K for Pt/$SiO_2$—$Al_2O_3$, and at a temperature of 533 K for the Pd/$Al_2O_3$ and Pt/$Al_2O_3$ catalysts. The temperature was ramped from room temperature to the desired reduction temperature over a period of 8 h and held at the final temperature for 2 h. The irreversible CO uptakes at 300 K (measured on a standard gas adsorption apparatus, see Spiewak, Shen & Dumesic (1995) *J. Phys. Chem.* 99:17640) were 101, 151 and 141 $\mu$moles/$g^{-1}$ of catalyst for the 3 wt % Pt/$Al_2O_3$, 3 wt % Pd/$Al_2O_3$ and 4 wt % Pt/$SiO_2$—$Al_2O_3$ catalysts, respectively.

A mixed Mg—Al-oxide catalyst with Mg/Al atomic ratio=2 was prepared by adding $Mg(NO_3)_2 \cdot 6H_2O$ (0.188 mol) and $Al(NO_3)_3 \cdot 9H_2O$ (0.093 mol) to 200 g of $H_2O$. A second solution containing NaOH (0.438 mol) and $Na_2CO_3$ (0.113 mol) in 200 g of $H_2O$ was slowly added to the Mg/Al aqueous solution in a 1000 ml flask with constant stirring over a period of 3 h. All chemicals were purchased from Aldrich. The pH of the solution was maintained at 11.0 by adding additional NaOH solution (25 wt %) when required. This solution was then heated to 338 K for 18 h. A precipitate formed which was subsequently filtered and washed with DI water until the sodium (Na) content of the filtrate was below 10 ppm as measured by inductively coupled plasma ("ICP") analysis. The precipitate was dried in an oven at 353 K for 12 h to obtain the hydrotalcite. Calcination of the hydrotalcite was carried out in flowing 02 (GHSV ~400 $h^{-1}$), during which the temperature was ramped from room temperature to 723 K over 2 h and then held at 723 K for 8 h. The Mg—Al oxide catalyst thus formed was used to carry out aldol condensation reactions, as described below.

The preferred magnesia-zirconia (MgO—$ZrO_2$) catalyst was synthesized using the sol-gel technique described by Aramendia et al. (2004) *J Mol. Catal. A: Chem.* 218:81 and Aramendia et al. (2004) *Colloids Surf., A* 234:17, starting with magnesium nitrate ($Mg(NO_3)_2 \cdot 6H_2O$, Aldrich) and zirconyl nitrate ($ZrO(NO_3)_2$, Aldrich). The catalyst was prepared by dissolving 50.9 g of magnesium nitrate and 4.04 g of zirconyl nitrate in 1 liter of deionized (DI) water. The mixture was stirred at room temperature, and NaOH (25 wt %) solution was added until the pH was equal to 10. The gel was aged for 72 h and subsequently vacuum filtered. The precipitate formed was washed with DI water until the Na ion concentration in the filtrate was below 10 ppm, as measured by ICP analysis (PerkinElmer Plasma 400 ICP Emission Spectrometer, PerkinElmer, Fremont, Calif.). The filtrate was then dried in an oven at 393 K from 16 to 24 h. Calcination of the catalyst was carried out in $O_2$ (~100 $cm^3$ (NTP) $min^{-1}$) with a 3 h ramp and a 3 h hold to 873 K. The catalyst thus obtained was used for the initial activity runs (see FIG. 3) for aldol condensation of HMF with acetone, using a HMF:acetone molar ratio of 1:10.

A 5 wt % Pd/MgO—$ZrO_2$ catalyst was prepared by incipient wetness impregnation of Pd (using 5 wt % Pd in tetraaminepalladium (II) nitrate solution from Strem Chemicals) onto the above-mentioned MgO—$ZrO_2$ support. The impregnated catalyst was then calcined in flowing $O_2$ (~120 $cm^3$ (NTP) $min^{-1}$) with a 2 h ramp and a 2 h hold to 723 K. The catalyst so obtained was used for all the aldol condensation and sequential hydrogenation runs described herein.

The irreversible uptakes of CO and $CO_2$ on catalysts at 300 K were measured using a standard gas adsorption apparatus as described in Spiewak, Shen & Dumesic (1995) *J. Phys. Chem.* 99:17640). Prior to CO or $CO_2$ adsorption measurements, the catalyst was reduced in flowing $H_2$, with an 8 h ramp and 2 h hold at 393 K. After reduction, the temperature was ramped to 573 K for 30 min and held for 30 min, while evacuating the cell. The cell was cooled to room temperature, and the adsorbant was then dosed onto the catalyst in 10 to 15 doses until the equilibrium pressure was approximately 5 Torr. Gas in the cell was then evacuated for 30 min at room temperature to a pressure of $10^{-6}$ Torr, and the adsorbant was again dosed on the sample to determine the amount of reversibly adsorbed CO or $CO_2$. Irreversible uptake was determined by subtracting the second isotherm from the first. Brunauer-Emmett-Teller ("BET") surface areas were measured by $N_2$ adsorption at 77 K on this same system. (Regarding BET surface area measurements, see Brunauer, Emmett and Teller (1938) *J. Am. Chem. Soc.* 60:309.)

X-ray diffraction data were collected with a Cu K$\alpha$ source using a Scintag PADV diffractometer operating at 40.0 mA and 35.0 kV. Diffraction patterns were collected in continuous scan mode with steps of 0.02 deg $sec^{-1}$. The Scherrer equation was used to estimate crystal size.

A thermo-gravimetric analyzer from Netzsch Thermal Analysis (model TG 209 with a TASC 414/3 temperature controller) was used to analyze the amount of coke formed on the catalyst surface. Approximately 4.5 mg of spent catalyst was weighed and heated to 423 K in 13 min in the presence of flowing $O_2$. The temperature was held at that point for an additional 30 min and ramped to 723 K at a rate of 10 K $min^{-1}$. The amount of carbon on the catalyst was obtained by comparing thermogravimetric analysis ("TGA") data for fresh versus spent catalyst samples.

As shown in Table 3, metal sites (~50±2 $\mu$mol/g), surface area (~300+30 $m^2$/g), and average particle size (~11+2 nm) for before and after reaction did not change appreciably, while the phases found (MgO (200, 220), $ZrO_2$ (111, 220)) remained constant. Hence X-ray diffraction (XRD), CO chemisorption and BET surface area measurements show that the catalyst has excellent recycling ability and hydrothermal stability. Base catalyst sites were found to be ~103 $\mu$mol/g.

TABLE 3

Characterization of 5 wt % Pd/MgO—ZrO$_2$. All catalysts were
calcined and reduced before chemisorption, BET, and XRD analysis.
Mean diameter by XRD was estimated by line broadening of powder
XRD peaks using the Scherrer equation (±1 nm).

| Chemisorption & BET | Catalyst Before Reaction | After Fur:Ace Reaction | After HMF:Ace Reaction |
|---|---|---|---|
| Metal Sites, μmol/g | 49.0 | 51.7 | 48.8 |
| Base Sites, μmol/g | 103 | — | — |
| Surface Area, m$^2$/g | 292 | 329 | 299 |

| XRD, Identified Phase, Miller Indice, & 2θ | Average Particle Size, Before Reaction/nm | Average Particle Size, After Fur:Ace (run 1)/nm | Average Particle Size, After HMF:Ace (run 15)/nm |
|---|---|---|---|
| MgO (200), 2θ = 30.65° | 9 | 10 | 9 |
| MgO (220), 2θ = 42.79° | 10 | 12 | 11 |
| ZrO$_2$ (111), 2θ = 51.08° | 10 | 13 | 12 |
| ZrO$_2$ (220), 2θ = 62.05° | 10 | 10 | 13 |

Four-phase Dehydration/Hydrogenation Reactor: FIG. 1 shows the four-phase dehydration/hydrogenation (four-phase D/H) reactor used to conduct the reaction kinetics studies. Pelletized catalyst was loaded into a ½ or ¼" outside diameter tubular stainless steel reactor. The catalyst bed was contained in the tubular reactor between two end-plugs of quartz wool (Alltech, a division of Grace Davison Discovery Sciences, Deerfield, Ill.). Type-K thermocouples (Omega) attached to the outside of the reactor were used to measure the reactor temperature, which was controlled with a series 16A type temperature controller (Dwyer Instruments). Prior to reaction kinetics studies, the calcined catalyst was reduced in flowing H$_2$ as outlined above in the catalyst preparation section. The flow rate of H$_2$ was controlled with mass-flow meters (5850 Brooks Instruments). An HPLC pump (Model 301, Alltech) was used to introduce the aqueous feed solution into the upflow reactor. The hexadecane feed was also introduced to the reactor with an HPLC pump (Model 301, Alltech). The effluent from the reactor was water-cooled in a double-pipe heat exchanger. The effluent liquid was drained periodically for total organic carbon (TOC) analysis (Shimadzu TOC-6001 with autosampler) (Shimadzu Corporation, Kyoto, Japan) of the aqueous phase and for GC analysis of the organic phase (Shimadzu GC-2010 with an flame ionization detector ("FID" detector) and a DB-5 column from Alltech). Each feed was tested for at least 20 h time-on-stream.

The effluent gas stream passed through a back-pressure regulator (GO Regulator, Spartanburg, S.C., Model BP-60) which controlled the system pressure. This off-gas stream was analyzed with two different gas chromatographs: a) the H$_2$ and CH$_4$ were analyzed with a Carle GC (Carle Instruments, Inc., Fullerton, Calif., Series 400 AGC) using a TCD detector and a Porapak Q packed column (Alltech); and b) the CO$_2$ and alkanes heavier than methane were analyzed in a Varian GC-MS (model Saturn 3; Varian, Inc., Palo Alto, Calif.) using a FID detector and a GS-Q capillary column (J&W Scientific, now Agilent Technologies, Santa Clara, Calif.).

Tetrahydrofurfural Preparation: Tetrahydrofurfural-2-aldehyde (THF2A) was prepared by selective dehydrogenation of tetrahydrofurfural alcohol (Aldrich) in a gas-phase fixed-bed reactor using a 10 wt % Cu/SiO$_2$ catalyst (Cab-o-sil), prepared by incipient wetness impregnation as described in Cortright, Sanchez-Castillo & Dumesic (2002) *Appl. Catal. B* 39:353. The feed was introduced to the reactor by an HPLC pump (Model 301, Alltech) at a LHSV=0.67 h$^{-1}$ (LHSV defined as g$_{feed}$/(h g$_{catalyst}$), and a helium sweep gas (GHSV=~2500 h$^{-1}$) was used to dilute the feed. The catalyst deactivated continuously during reaction because of coke formation; therefore, to maintain high catalytic activity the temperature of the reaction was increased from 573 to 673 K in 50 K increments every 45 min. Condensable species were separated from the sweep gas in an ice-bath glass condenser. The catalyst was regenerated in an air stream at a GHSV of ~2500 h$^{-1}$ for 30 min at 673 K after every 2.25 h of operation. Hydrogen at a GHSV of ~2500 h$^{-1}$ was then fed to the reactor to re-reduce the catalyst.

Aldol Condensation: Aldol condensation reactions were carried out in batch mode at room temperature with the catalysts described above. Different feed solutions were prepared with appropriate molar ratios of the co-reactants, as given in Table 5. The weight ratio of organics to catalyst ranged from 2 to 10. Reactant disappearance was traced versus time using HPLC analysis (Waters 2690 system (Waters Corporation, Milford, Mass.) with a Zorbax SB-C18 5 μm column from Agilent and PDA 960 and RI 410 detectors).

Aldol condensation reactions were carried out over the catalyst in the aqueous phase and stopped by filtering the catalyst from the reaction mixture at different times ranging from 2 to 48 h, except for the HMF:Ace (1:1)-3 and HMF:Fur:Ace (1:1:2) feeds in which filtration was done after hydrogenation. The pH of the filtered solutions was approximately 10, and further experiments indicated that the condensation reactions continued to occur in the filtered solution at a rate 10 times slower than with the solid base catalyst present. In addition, the mixed Mg—Al-oxide catalyst lost significant activity upon recycling in sequential batch reactor runs.

In contrast, it was found that a Mg—Zr-oxide catalyst has considerably better stability for aqueous-phase aldol condensation reactions than the Mg—Al-oxide catalyst, with negligible loss of catalytic activity upon recycling. Also, when the Mg—Zr-oxide catalyst was used, the pH of the filtered solution was the same as the pH of the feed solution (pH of 6), thereby minimizing the contribution of aldol condensation reactions occurring homogeneously in the aqueous phase. Similar alkane selectivities were obtained for feeds condensed with Mg—Zr-oxide and Mg—Al-oxide catalysts.

Aldol condensation reactions of HMF:Ace (1:1)-1 and HMF:Ace (1:1)-2 were carried out initially in water, resulting in formation of insoluble products. The precipitate thus formed was dissolved in excess methanol (a methanol to water weight ratio of 2 to 1), and then hydrogenated to form the water-soluble feed to the four-phase D/H reactor. Fur:Ace (2:1) was prepared by condensing furfural-acetone (Aldrich) with furfural. The reaction was carried out by mixing 2.1 g furfural, 3.0 g furfural-acetone, 0.6 g NaOH pellets, 80 g water and 80 g methanol in a well-stirred glass reactor at room temperature for 10 h. The solution was then neutralized with HCl and the solvent was evaporated. The resulting solid product was washed with $H_2O$ to remove NaCl.

Hydrogenation of Feeds: Aqueous solutions of the condensed feeds were hydrogenated in a batch Parr Reactor (Model # 4566) prior to being fed into the four-phase D/H reactor. Feeds were hydrogenated using a 3 wt % $Pd/Al_2O_3$ catalyst at 393 K, 55 bar and a stirring speed of 570 rpm. The amount of catalyst, solvent and reaction time of hydrogenation reactions are listed in Table 6.

Reaction System and Analysis Method: All reactions (see Table 4) were carried out in a Parr batch reactor (Model # 4566) with an external temperature and stirring controller (Model # 4836). The reactor was initially loaded with the reaction mixture and air was purged by adding helium up to 55 bar three times before starting the condensation reaction. The reactor was then pressurized to 8 bar with He, heated to the reaction temperature, and stirred at 1000 rpm. After reaching the reaction temperature, the reactor was pressurized to 10 bar. Aldol condensation was stopped after 24 to 26 h of reaction time, and the reactor was then cooled to room temperature. The hydrogenation reaction was started by a similar purging procedure with $H_2$ and pressurizing the reactor to 44 bar before heating. The stirring speed was maintained at 1000 rpm and the reactor was heated to 393 K at which time $H_2$ was added to reach a pressure of 55 bar.

Hydrogenation of the furfural:acetone 1:1 system was complete in 4-6 h at 393 K, and this temperature was employed for all hydrogenation runs with no further optimization. Hydrogenation was stopped after a constant carbon yield in the aqueous phase was reached, which was ensured for all runs by allowing the reaction to proceed for 24 h with monitoring. For Table 4, run 13, after condensation was complete, the aqueous layer was evaporated, leaving catalyst, precipitated monomer, and dimer in the reactor. At this point, hexadecane was added in a volume equal to that of the evaporated aqueous layer and the subsequent hydrogenation reaction was conducted.

Samples were withdrawn from the sampling port during the condensation and hydrogenation reaction. Samples were filtered (using a 0.2 μm polyethersulfone ("PES") syringe membrane filter) before being analyzed by GC (Shimadzu GC-2010 with a FID detector and a DB-5 column from Alltech). For catalyst recycle experiments without calcination (Table 1 runs 2 & 3), the reaction mixture was filtered after the hydrogenation run and the catalyst was dried in an oven at 393 K for 12 to 16 h before reuse. Additionally for the recycle run with catalyst calcination (Table 4, run 4), the catalyst was calcined after use as described above for $Pd/MgO-ZrO_2$. The ICP analysis for Na, Mg and Pd in the final reaction mixture showed negligible leaching of the catalyst components. Total organic carbon (TOC) analysis (Shimadzu TOC-6001 with autosampler) was performed on final reaction mixtures to quantify the total carbon present and to calibrate the GC for reaction products. Furfural:acetone dehydrated monomer (4-(2-furyl)-3-buten-2-one) was hydrogenated for calibration purposes. The self-condensation product of acetone was not identified in HPLC during the condensation runs as confirmed by running standards of diacetone alcohol (4-hydroxy-4-methyl-2-pentanone). Both chemicals were purchased from Aldrich.

The initial studies (see FIG. 3) of aldol condensation with HMF:acetone (molar ratio of 1:10) were carried out in 50 ml glass reactor vessels using an oil bath to control the reaction temperature. Regular samples were withdrawn, filtered (using 0.2 μm PES syringe membrane filter) and the HMF disappearance was monitored using HPLC (Waters 2695 system with a Zorbax SB-C18 5 μm column from Agilent and PDA 960 and RI 410 detectors).

Overall carbon yield and selectivity were calculated based on $C_5$ (for furfural) or $C_6$ (for HMF) units. For furfural:acetone reactions:

$$\text{Overall Carbon Yield \%} = \frac{3*\text{moles } C_3 + 5*\text{moles } C_5 + 8*\text{moles } C_8 + 13*\text{moles } C_{13}}{3*\text{moles } C_3 \, fed + 5*\text{moles } C_5 \, fed} * 100$$

$$C_5 \text{ Selectivity\%} = \frac{\text{moles } C_5}{\text{moles } C_5 + \text{moles } C_8 + 2*\text{moles } C_{13}} * 100$$

An analogous definition applies for HMF:acetone reactions on a $C_6$ basis.

TABLE 4

Experimental data for aldol condensation and hydrogenation batch reactions. All the runs were carried out in a Parr batch reactor over 5 wt % Pd/MgO—ZrO$_2$, 5 wt % organics in the aqueous solution, condensation pressure of 10 bar, hydrogenation time of 24 h, temperature of 393 K, and pressure of 55 bar (except run 12 using 0.5 wt % Pd and hydrogenated for 40 h). Recycle runs (Run 1-4) were carried out using the same catalyst, 1$^{st}$ run with fresh catalyst, 2$^{nd}$ and 3$^{rd}$ runs with recycled catalyst without calcinations, and 4$^{th}$ run with calcination.

| Run # | Feed | Molar Ratio | Org/Cat[a] | Time [h][b] | Temperature [K][c] | Volume [ml] | Disappearance [%] Furfural | Selectivity C$_5$ units [%] C$_5$ | C$_8$ | C$_{13}$ | Overall Carbon Yield [%] |
|---|---|---|---|---|---|---|---|---|---|---|---|
| 1 | Fur:Ace [1$^{st}$] | 1:1 | 6 | 26 | 326 | 250 | 79 | 23 | 34 | 43 | 91 |
| 2 | Fur:Ace [2$^{nd}$] | 1:1 | 6 | 26 | 326 | 200 | 58 | 43 | 31 | 26 | 93 |
| 3 | Fur:Ace [3$^{rd}$] | 1:1 | 6 | 26 | 326 | 125 | 58 | 45 | 31 | 24 | 90 |
| 4 | Fur:Ace [4$^{th}$] | 1:1 | 9 | 26 | 326 | 90 | 76 | 25 | 32 | 43 | 91 |

TABLE 4-continued

Experimental data for aldol condensation and hydrogenation batch reactions. All the runs were carried out in a Parr batch reactor over 5 wt % Pd/MgO—ZrO$_2$, 5 wt % organics in the aqueous solution, condensation pressure of 10 bar, hydrogenation time of 24 h, temperature of 393 K, and pressure of 55 bar (except run 12 using 0.5 wt % Pd and hydrogenated for 40 h). Recycle runs (Run 1-4) were carried out using the same catalyst, 1$^{st}$ run with fresh catalyst, 2$^{nd}$ and 3$^{rd}$ runs with recycled catalyst without calcinations, and 4$^{th}$ run with calcination.

| | | | | | | | | | | |
|---|---|---|---|---|---|---|---|---|---|---|
| 5 | Fur::Ace | 1:1 | 6 | 24 | 353 | 100 | 95 | 5 | 35 | 60 | 88 |
| 6 | Fur:Ace | 1:1 | 6 | 26 | 393 | 100 | 98 | 3 | 35 | 62 | 80 |
| 7 | Fur:Ace | 1:9 | 6 | 24 | 353 | 100 | 96 | 4 | 67 | 29 | 76 |
| 8 | Fur:Ace | 2:1 | 6 | 24 | 353 | 100 | 66 | 37 | 15 | 48 | 91 |
| 9 | Fur:Ace | 2:1 | 6 | 56 | 353 | 100 | 86 | 16 | 12 | 72 | 85 |
| 10 | Fur:Ace | 1:1 | 18 | 25 | 393 | 100 | 90 | 11 | 30 | 59 | 85 |
| 11 | Fur:Ace | 1:1 | 36 | 26 | 393 | 100 | 88 | 14 | 32 | 54 | 82 |
| 12 | Fur:Ace - 0.5% Pd[d] | 1:1 | 6 | 25 | 393 | 112 | 98 | 2 | 33 | 65 | 82 |
| 13 | FurAce - hexadec[e] | 1:1 | 6 | 24 | 353 | 100 | 100 | 0 | 15 | 85 | 71 |

| | | | | | | | HMF | C$_6$ units [%] | | |
|---|---|---|---|---|---|---|---|---|---|---|
| | | | | | | | | C$_6$ | C$_9$ | C$_{15}$ |
| 14 | HMF:Ace | 1:1 | 6 | 26 | 298 | 70 | 51 | 42 | 20 | 38 | 100 |
| 15 | HMF:Ace | 1:1 | 6 | 26 | 326 | 100 | 79 | 21 | 18 | 61 | 94 |
| 16 | HMF:Ace | 1:1 | 6 | 26 | 353 | 100 | 88 | 14 | 21 | 65 | 84 |
| 17 | HMF:Ace | 1:1 | 6 | 26 | 393 | 100 | 93 | 11 | 38 | 51 | 67 |

[a]Organic to catalyst ratio by mass
[b]Time for aldol condensation
[c]Reaction temperature for aldol condensation
[d]Reaction carried out over 0.5 wt % Pd/MgO—ZrO$_2$
[e]Aldol condensation carried out in water and hydrogenation conducted in hexadecane solvent at 393 K, 55 bar.

Sample Energy Calculations for Corn to Alkanes: The energy required to produce ethanol from corn (including corn production, corn transportation, ethanol conversion and ethanol transportation) has been reported to be 77,228 BTU/gal$_{ethanol}$. See Shapouri, Duffield & Wang, "The Energy Balance of Corn: An Update," No. 814, U.S. Department of Agriculture, Office of the Chief Economist, 2002. The total energy required (taking into account the EPA's efficiency factor for the energy used to mine and transport coal) for the ethanol conversion plant is 51,779 BTU/gal$_{ethanol}$ (Id.) of which the actual thermal energy is 36,000 BTU/gal$_{ethanol}$. The actual thermal energy required for the distillation process is reported to be 18,000 to 19,800 BTU/gal$_{ethanol}$. See R. Katzen et al. in "Fuels from Biomass and Wastes," Klass & Emert, Eds. (Ann Arbor Science, Ann Arbor, © 1981) pp. 393-402. In short, over half of the energy in the ethanol conversion process is used to distill ethanol from water. Eliminating the distillation process in ethanol production, and assuming that the distillation process accounts for 50% of the energy in the ethanol conversion process, then the energy required to produce ethanol from corn would be 51,000 BTU/gal$_{ethanol}$. Using the ethanol (328 L$_{ethanol}$/ton$_{biomass}$, 1 ton=2,000 lb$_m$) and sugar yields (0.82 ton$_{sugar}$/ton$_{biomass}$) as reported by Klass (see D. L. Klass, "Biomass for Renewable Energy, Fuels and Chemicals," Academic Press, San Diego, © 1998), it is estimated that the energy required for conversion of corn to ethanol (excluding distillation) is equal to 5,400,000 BTU/ton$_{sugar}$, and it is assumed that this value is also equal to the energy required to convert corn to alkanes. Using a value of 2,540 kJ/mole for the heat of combustion of glucose and assuming that sugars are converted to alkanes as given by a stoichiometry analogous to equation 3, then approximately 96% of the energy of the sugar would be retained in the alkane product, giving a heating value for the alkanes of 11,600,000 BTU/ton$_{sugar}$. The overall energy efficiency for conversion of alkanes to corn can now be calculated to be 2.2 by dividing the heating value of the alkanes (11,600,000 BTU/ton$_{sugar}$) by the energy required to produce alkanes (5,400,000 BTU/ton$_{sugar}$). The overall energy efficiency for both conversion of corn to ethanol or corn to alkanes can be increased further by using co-product energy credits. See Shapouri, Duffield & Wang, "The Energy Balance of Corn: An Update," No. 814, U.S. Department of Agriculture, Office of the Chief Economist, 2002.

TABLE 5

Aldol condensation of biomass derived molecules. Aldol condensation reactions were carried out at room temperature with Mg—Al-oxide catalysts. All feed molecules were purchased from Aldrich, except for THF2A which was prepared from tetrahydrofurfuryl alcohol (Aldrich). All reactions, except for HMF:Ace (1:1)-1 and HMF:Ace (1:1)-2, were conducted in aqueous solutions. Feed key: SC = self condensed; Fur = furfural; Ace = acetone; HMF = 5-hydroxymethylfurfural; DHA = dihydroxyacetone; HA = hydroxyacetone; GHA = glyceraldehyde; THF3A = tetrahydrofuran-3 carboxyaldehyde; THF2A = tetrahydrofuran-2 carboxyaldehyde. Numbers listed in parentheses indicate molar ratio of feeds. Wt (%) is weight percent organics in aqueous feed solution. Org/cat is organic to catalyst weight ratio. Diss (%) is disappearance of HMF, furfural or self condensed feeds tracked by HPLC. C$_{out}$/C$_{in}$ is outlet carbon divided by inlet carbon as measured by TOC. For reactions carried out with methanol this measurement could not be made. For HMF:Ace (1:1)-3 and HMF:Fur:Ace (1:1:2) feeds the outlet carbon in the aqueous feed was measured after hydrogenation.

| Feed | Wt (%) | Org/cat | Time (h) | Diss (%) | C$_{out}$/C$_{in}$ (TOC) |
|---|---|---|---|---|---|
| HMF:Ace (1:10) | 11.2 | 6.5 | 5.0 | 100 | 0.90 |
| HMF:Ace (1:1)-1 | 5 | 6 | 9.0 | 80 | N.A. |
| HMF:Ace (1:1)-2 | 5 | 3 | 9.0 | 100 | N.A. |
| HMF:Ace (1:1)-3 | 5 | 6 | 20.9 | N.A. | 0.89 |
| HMF:Fur:Ace (1:1:2) | 5 | 6 | 31.0 | N.A. | 0.93 |
| Fur:DHA (2:1) | 5 | 6 | 4.5 | 58 | 0.90 |
| Fur:DHA (1:1) | 5 | 6 | 2.5 | 68 | 1.00 |
| Fur:DHA (1:3) | 5 | 6 | 2.0 | 89 | 0.98 |
| Fur:HA (1:3) | 5 | 6 | 4.5 | 100 | 1.00 |
| Fur:GHA (1:1) | 5 | 6 | 2.5 | 82 | 0.83 |
| HMF:DHA (1:1) | 5 | 6 | 2.2 | 89 | 0.97 |
| SC DHA | 5 | 6 | 20.0 | 100 | 1.03 |
| SC THF3A | 25 | 10 | 9.0 | 71 | 0.96 |
| SC THF2A | 10 | 2 | 48.0 | 84 | 0.80 |

TABLE 6

Hydrogenation of biomass derived molecules. (All hydrogenation reactions carried out with a $Pd/Al_2O_3$ catalyst at 393 K and 55 bar in a stainless steel batch reactor. See Table 5 for feed key.)

| Feed | Solvent | Wt (%) | Catalyst/Feed Weight Ratio | Reaction Time (h) |
|---|---|---|---|---|
| Furoin | MeOH | 3.2 | 0.45 | 2 |
| Fur:Ace (1:1)-1 | MeOH | 3.8 | 0.40 | 1 |
| Fur:Ace (1:1) org | MeOH | 5.3 | 0.45 | 22 |
| Fur:Ace (1:1)-3 | $H_2O$ | 14.0 | 0.09 | 25 |
| Fur:Ace (2:1) | $MeOH/H_2O$ | 2.3 | 0.40 | 1 |
| HMF:Ace (1:1)-1 | $MeOH/H_2O$ | 2.0 | 0.56 | 1 |
| HMF:Ace (1:1)-2 | $MeOH/H_2O$ | 1.8 | 0.65 | 1 |
| HMF:Ace (1:1)-3 | $H_2O$ | 1.8 | 0.24 | 8 |
| HMF:Ace (1:10) | $H_2O$ | 9.5 | 0.45 | 22 |
| HMF:Fur:Ace (1:1:2) | $H_2O$ | 1.9 | 0.33 | 14 |
| Fur:DHA (2:1) | $H_2O$ | 1.8 | 0.45 | 22 |
| Fur:DHA (1:1) | $H_2O$ | 2.0 | 0.45 | 22 |
| Fur:DHA (1:3) | $H_2O$ | 1.7 | 0.45 | 22 |
| Fur:HA (1:3) | $H_2O$ | 2.0 | 0.45 | 22 |
| Fur:GHA (1:1) | $H_2O$ | 1.6 | 0.45 | 22 |
| HMF:DHA (1:1) | $H_2O$ | 2.0 | 0.45 | 22 |
| SC DHA | $H_2O$ | 5.0 | 0.45 | 22 |
| SC THF3A | $H_2O$ | 5.0 | 0.45 | 22 |
| SC THF2A | $H_2O$ | 3.9 | 0.45 | 22 |

TABLE 7

Conversion and process conditions for 4-phase dehydration/hydrogenation of biomass-derived molecules. All four-phase D/H reactions were carried out at 523 to 538 K, 52 to 60 bar and $H_2$ gas hourly space velocity (v/v) of 1000 to 3000 $h^{-1}$. For the sorbitol feed, a physical mixture of 1.5 g USY zeolite and 2.9 g 3 wt % $Pt/Al_2O_3$ catalyst was used, which had similar activity and selectivity to a 4 wt % $Pt/SiO_2$—$Al_2O_3$ catalyst. For all other feeds, a 4 wt % $Pt/SiO_2$—$Al_2O_3$ catalysts was used. Each experimental point was collected after 20 h time-on-stream. Condensed feeds were prepared by aldol condensation at room temperature using Mg—Al-oxide and NaOH catalysts. See Table 5 for feed key. Numbers listed in parentheses indicate molar ratio of feeds. All feeds (except sorbitol) were hydrogenated in a Parr reactor with a $Pd/Al_2O_3$ catalyst prior to conversion in the four-phase D/H reactor. Entries S5 to S7 and S9 to S11 were hydrogenated in methanol or a methanol/water mixture, with all other feeds being hydrogenated in $H_2O$. Abbreviations: Wt (%) refers to weight percent organics in aqueous feed solution. WHSV is weight hourly space velocity; mass of aqueous feed solution per mass of catalyst per hour. Org/Aq is the organic (hexadecane) to aqueous volumetric feed ratio.

| Entry | Feed | Wt (%) | WHSV ($h^{-1}$) | Org/Aq | % Carbon in Phase Org | Gas | Aq |
|---|---|---|---|---|---|---|---|
| S1 | Sorbitol | 5.0 | 1.26 | 0.0 | — | 86.8 | 18.6 |
| S2 | | 5.0 | 1.26 | 1.0 | 41.3 | 41.0 | 11.9 |
| S3 | | 5.0 | 1.26 | 3.0 | 38.5 | 31.2 | 15.5 |
| S4 | | 1.0 | 1.26 | 3.0 | 35.7 | 46.4 | 10.3 |
| S5 | Furoin | 2.0 | 0.26 | 3.0 | 69.2 | 18.5 | 2.3 |
| S6 | Fur:Ace (1:1)-1 | 1.9 | 0.26 | 3.0 | 100.0 | 6.3 | 1.6 |
| S7 | Fur:Ace (1:1) org* | 5.0 | 0.51 | ∞ | 73.2 | 7.8 | NA |
| S8 | Fur:Ace (1:1)-3 | 12.5 | 0.29 | 3.0 | 91.2 | 4.1 | 0.7 |
| S9 | Fur:Ace (2:1) | 1.0 | 0.29 | 3.0 | 79.0 | 2.4 | 0.8 |
| S10 | HMF:Ace (1:1)-1 | 1.8 | 0.25 | 3.0 | 66.1 | 15.7 | 1.5 |
| S11 | HMF:Ace (1:1)-2† | 1.9 | 0.26 | 3.0 | 69.5 | 7.7 | 0.9 |
| S12 | HMF:Ace (1:1)-3 | 1.8 | 0.29 | 3.0 | 53.3 | 31.1 | 2.3 |
| S13 | HMF:Ace (1:10) | 9.5 | 0.35 | 0.7 | 77.2 | 10.3 | 20.0 |
| S14 | HMF:Fur:Ace (1:1:2) | 1.9 | 0.29 | 3.0 | 48.5 | 27.8 | 3.1 |
| S15 | Fur:DHA (2:1) | 1.8 | 0.20 | 3.0 | 46.6 | 47.9 | 5.2 |
| S16 | Fur:DHA (1:1) | 2.0 | 0.20 | 3.0 | 43.9 | 47.7 | 5.3 |
| S17 | Fur:DHA (1:3) | 1.7 | 0.20 | 3.0 | 35.9 | 58.9 | 10.5 |
| S18 | Fur:HA (1:3) | 2.0 | 0.25 | 3.0 | 29.6 | 55.6 | 16.7 |
| S19 | Fur:GHA (1:1) | 1.6 | 0.25 | 3.0 | 48.6 | 47.0 | 8.7 |
| S20 | HMF:DHA (1:1) | 2.0 | 0.20 | 3.0 | 44.0 | 41.8 | 5.3 |
| S21 | SC DHA | 5.0 | 0.27 | 3.0 | 19.1 | 59.5 | 11.0 |
| S22 | SC THF3A | 5.0 | 0.35 | 0.7 | 53.2 | 44.1 | 4.2 |
| S23 | SC THF2A | 3.9 | 0.35 | 0.7 | 47.9 | 20.8 | 13.0 |

*Fur:Ace (1:1) org was added to the hexadecane feed and no aqueous flow was used for this feed.
†This feed was condensed with twice the amount of Mg—Al-oxide than the feed above it (Entry S10).

TABLE 8

Alkane and $CO_2$ selectivities from 4-phase dehydration/hydrogenation of biomass derived-molecules. (Table 7 contains relevant process conditions and conversion data. Table 5 contains feed key. Selectivity = (moles product × number of carbon atoms in product)/(total moles of carbon atoms in products) × 100. The selectivity only takes into account the products in the organic and gas phases. Alkane products are mostly straight chain, except for the SC THF3A and SC THF2A feeds. At lower conversions small amounts of alcohols (<10% of total products) are also observed in the organic phase.)

| | | Alkane and $CO_2$ Selectivities (%) | | | | | | | | | | | | | | |
|---|---|---|---|---|---|---|---|---|---|---|---|---|---|---|---|---|
| Entry | Feed | $CO_2$ | $C_1$ | $C_2$ | $C_3$ | $C_4$ | $C_5$ | $C_6$ | $C_7$ | $C_8$ | $C_9$ | $C_{10}$ | $C_{11}$ | $C_{12}$ | $C_{13}$ | $C_{14}$ | $C_{15}$ |
| S1 | Sorbitol | 14.6 | 3.6 | 4.7 | 8.5 | 11.6 | 20.5 | 36.6 | 0.0 | 0.0 | 0.0 | 0.0 | 0.0 | 0.0 | 0.0 | 0.0 | 0.0 |
| S2 | | 15.0 | 2.2 | 4.7 | 8.8 | 12.3 | 19.4 | 37.7 | 0.0 | 0.0 | 0.0 | 0.0 | 0.0 | 0.0 | 0.0 | 0.0 | 0.0 |
| S3 | | 15.3 | 2.1 | 5.4 | 8.4 | 8.7 | 23.4 | 36.5 | 0.0 | 0.0 | 0.1 | 0.0 | 0.0 | 0.0 | 0.0 | 0.0 | 0.0 |
| S4 | | 20.4 | 3.1 | 9.1 | 10.1 | 10.3 | 21.3 | 25.3 | 0.0 | 0.0 | 0.4 | 0.0 | 0.0 | 0.0 | 0.0 | 0.0 | 0.0 |
| S5 | Furoin | 5.2 | 5.2 | 0.0 | 2.8 | 8.0 | 9.2 | 1.8 | 0.3 | 5.4 | 26.2 | 34.0 | 0.7 | 0.3 | 0.3 | 0.4 | 0.2 |
| S6 | Fur:Ace (1:1)-1 | 1.8 | 2.2 | 0.0 | 0.0 | 0.1 | 0.2 | 0.3 | 15.0 | 77.7 | 0.6 | 0.2 | 0.4 | 0.3 | 0.4 | 0.4 | 0.4 |

TABLE 8-continued

Alkane and CO₂ selectivities from 4-phase dehydration/hydrogenation of biomass derived-molecules. (Table 7 contains relevant process conditions and conversion data. Table 5 contains feed key. Selectivity = (moles product × number of carbon atoms in product)/(total moles of carbon atoms in products) × 100. The selectivity only takes into account the products in the organic and gas phases. Alkane products are mostly straight chain, except for the SC THF3A and SC THF2A feeds. At lower conversions small amounts of alcohols (<10% of total products) are also observed in the organic phase.)

| Entry | Feed | $CO_2$ | $C_1$ | $C_2$ | $C_3$ | $C_4$ | $C_5$ | $C_6$ | $C_7$ | $C_8$ | $C_9$ | $C_{10}$ | $C_{11}$ | $C_{12}$ | $C_{13}$ | $C_{14}$ | $C_{15}$ |
|---|---|---|---|---|---|---|---|---|---|---|---|---|---|---|---|---|---|
| S7 | Fur:Ace (1:1) org | 0.0 | 4.7 | 0.2 | 1.7 | 1.8 | 2.0 | 1.9 | 4.5 | 71.4 | 2.4 | 2.2 | 2.2 | 2.1 | 2.4 | 0.6 | 0.0 |
| S8 | Fur:Ace (1:1)-3 | 1.7 | 0.4 | 0.0 | 0.1 | 0.1 | 0.1 | 0.2 | 17.1 | 64.4 | 7.4 | 5.8 | 2.5 | 0.1 | 0.1 | 0.1 | 0.0 |
| S9 | Fur:Ace (2:1) | 0.0 | 3.0 | 0.0 | 0.0 | 0.0 | 0.4 | 0.7 | 1.0 | 2.1 | 0.8 | 0.5 | 2.1 | 19.7 | 68.6 | 0.6 | 0.5 |
| S10 | HMF:Ace (1:1)-1* | 6.8 | 3.3 | 0.0 | 0.0 | 6.0 | 14.6 | 9.3 | 0.4 | 6.8 | 9.5 | 0.0 | 0.0 | 0.7 | 8.5 | 19.5 | 14.5 |
| S11 | HMF:Ace (1:1)-2* | 5.0 | 4.0 | 0.0 | 0.0 | 1.5 | 3.2 | 2.2 | 0.4 | 2.9 | 4.6 | 0.2 | 0.4 | 1.5 | 13.5 | 32.9 | 27.6 |
| S12 | HMF:Ace (1:1)-3 | 5.7 | 3.5 | 0.0 | 23.5 | 3.8 | 10.0 | 7.0 | 0.7 | 5.9 | 6.9 | 0.1 | 0.3 | 1.0 | 6.2 | 14.5 | 10.9 |
| S13 | HMF:Ace (1:10)† | 6.0 | 0.9 | 0.0 | 0.0 | 2.6 | 4.8 | 1.1 | 3.9 | 27.4 | 41.2 | 1.9 | 0.2 | 0.5 | 5.1 | 3.6 | 0.8 |
| S14 | HMF:Fur:Ace (1:1:2) | 4.0 | 3.0 | 0.0 | 25.3 | 3.8 | 7.2 | 3.3 | 2.5 | 10.2 | 5.6 | 0.0 | 1.0 | 4.8 | 14.3 | 10.8 | 4.4 |
| S15 | Fur:DHA (2:1) | 10.8 | 3.4 | 5.0 | 9.6 | 22.7 | 22.6 | 5.7 | 6.8 | 7.3 | 0.8 | 0.8 | 1.0 | 2.0 | 1.5 | 0.0 | 0.0 |
| S16 | Fur:DHA (1:1) | 9.6 | 3.7 | 10.1 | 10.7 | 18.3 | 21.0 | 6.6 | 8.0 | 7.4 | 1.5 | 0.8 | 0.5 | 1.3 | 0.4 | 0.2 | 0.0 |
| S17 | Fur:DHA (1:3) | 13.8 | 5.7 | 17.5 | 18.9 | 7.6 | 9.5 | 5.1 | 7.9 | 11.0 | 0.8 | 0.7 | 0.3 | 0.7 | 0.4 | 0.0 | 0.0 |
| S18 | Fur:HA (1:3) | 9.3 | 7.4 | 18.8 | 23.8 | 8.1 | 7.7 | 3.0 | 5.5 | 11.0 | 1.2 | 2.1 | 0.3 | 0.4 | 1.1 | 0.2 | 0.2 |
| S19 | Fur:GHA (1:1) | 10.4 | 4.8 | 5.6 | 9.3 | 18.5 | 22.0 | 8.5 | 5.7 | 9.6 | 1.7 | 0.9 | 0.6 | 0.4 | 0.3 | 1.4 | 0.3 |
| S20 | HMF:DHA (1:1) | 12.5 | 3.7 | 8.5 | 10.2 | 9.3 | 22.1 | 17.1 | 4.6 | 5.0 | 3.1 | 1.1 | 1.1 | 1.1 | 0.3 | 0.2 | 0.0 |
| S21 | SC DHA | 16.5 | 11.1 | 19.8 | 27.5 | 3.6 | 6.9 | 10.7 | 1.3 | 0.5 | 0.6 | 0.6 | 0.3 | 0.4 | 0.0 | 0.3 | 0.0 |
| S22 | SC THF3A‡ | 9.4 | 0.7 | 0.0 | 4.2 | 23.4 | 25.1 | 0.1 | 3.4 | 6.7 | 11.6 | 14.3 | 0.1 | 0.9 | 0.0 | 0.0 | 0.0 |
| S23 | SC THF2A§ | 11.4 | 1.3 | 0.0 | 5.1 | 15.1 | 9.9 | 0.5 | 5.2 | 13.0 | 17.7 | 19.4 | 0.3 | 0.9 | 0.3 | 0.0 | 0.0 |

*$C_3$ selectivity is zero because acetone was removed during separation of hydrogenated products from methanol-water solution.
†Propane is not included in the alkane selectivity calculation for this feed.
‡Liquid alkanes produced in this feed were mostly branched. The $C_{10}$ alkane was 3-methyl-5-dimethyl-heptane.
§Liquid alkanes produced in this feed were mostly branched. The $C_{10}$ alkane was 4-methylnonane.

Figure 9:
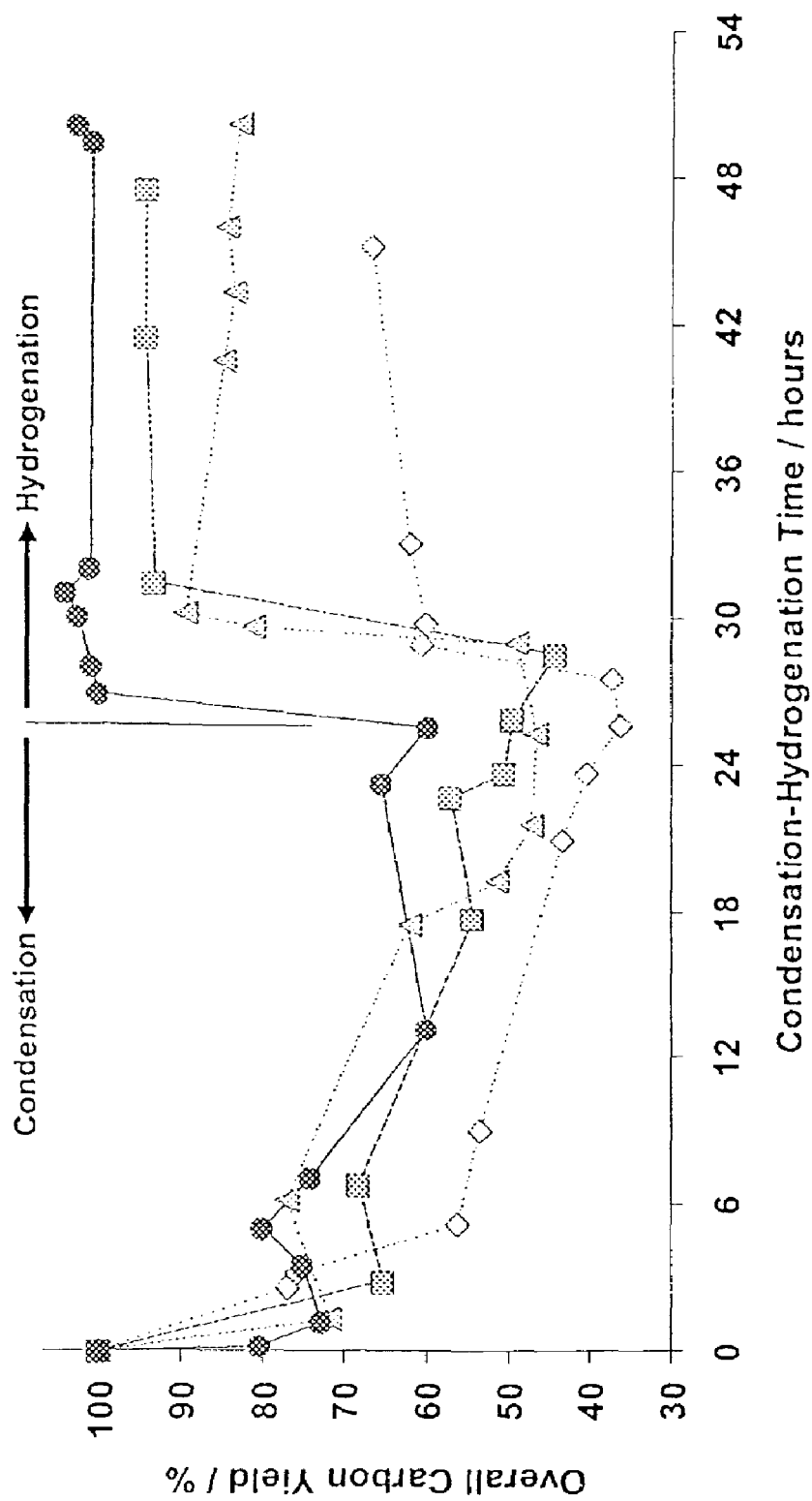
FIG. 9 is a graph depicting overall carbon yield in the aqueous phase versus time for aldol condensation at various temperatures of HMF with acetone (HMF:acetone molar ratio equal to 1:1), followed by hydrogenation at 393 K. Key: 298 K (black circles), 326 K (dark grey squares), 353 K (light grey triangles), 393 K (white diamonds).

FIG. 9 shows the aqueous phase concentration of carbon (normalized to the initial concentration of carbon in the batch reactor) versus time during aldol condensation over a bifunctional Pd/MgO—$ZrO_2$ catalyst at various temperatures, followed by sequential hydrogenation in the same batch reactor at 393 K. As aldol condensation proceeds, monomer and dimer species form and precipitate out of the aqueous solution, and the amount of carbon in the aqueous phase decreases accordingly. It is important to note that during this reaction the Pd on the catalyst is inert, because the performance of the Pd/MgO—$ZrO_2$ catalyst is identical to the performance of MgO—$ZrO_2$ during aldol condensation. Approximately 80% of the furfural has disappeared after a period of 24 h under these reaction conditions. The reactor was then pressurized to about 55 bar with hydrogen to initiate subsequent hydrogenation of the furan rings and thereby increase the solubility of monomer and dimer species in the aqueous phase. As seen in FIG. 9, this hydrogenation step leads to an increase in the concentration of carbon in the liquid phase. For example, while the carbon concentration in the aqueous phase after aldol condensation at 326 K decreases to about 44% of the initial carbon concentration, this value increases to about 94% after the hydrogenation step. FIG. 9 thus illustrates the ability of the bifunctional Pd/MgO—$ZrO_2$ catalyst to facilitate a single-reactor, aqueous phase process that combines aldol condensation with sequential hydrogenation, in which the aqueous phase carbon lost during the aldol condensation step is returned to the aqueous phase during the hydrogenation step. Table 4 shows the details of various runs conducted. TGA experiments identified 48%, 21% and 95% of the carbon missing from the carbon balance to be located on the catalyst for runs 1, 7 and 15 in Table 4, respectively. For run 7, furfural:acetone 1:9, roughly 63% of the missing carbon is caused by the initial purging of gas from the reactor (because of the high concentration and volatility of acetone), leading to an overall carbon yield equal to 96%.

As noted above, experiments were conducted to study the stability and recyclability of the bifunctional 5 wt % Pd/MgO—$ZrO_2$ for aldol condensation of acetone with furfural (molar ratio 1:1) at 326 K, followed by hydrogenation at 393 K. The catalyst was recycled for use in runs 2 and 3 without any intermediate regeneration, whereas the catalyst was subjected to a calcination treatment prior to run 4. FIG. 5 (Table 4, runs 1-4) shows that selectivity for the formation of the dimer adduct decreases by about 18% for recycle runs 2 and 3, while still maintaining good overall carbon yield (>90%), and returns to original levels for run 4. This result shows that the catalyst retains most of its activity and selectivity for at least three runs without requiring regeneration and can be completely regenerated through calcination. As shown in Table 3, metal sites (~50±2 μmol/g), surface area (~300±30 m²/g), and average particle size (~11±2 nm) for before and after reaction did not change appreciably, while the phases found (MgO (200, 220), $ZrO_2$ (111, 220)) remained constant. Hence XRD, CO chemisorption and BET measurements show that the catalyst has excellent recycling ability and hydrothermal stability. Aldol condensation does not take place homogeneously in the aqueous phase by dissolved basic species because the rate of aldol condensation was negligible after the MgO—$ZrO_2$ catalyst was removed from the aqueous solution. This further shows that the catalyst is stable.

Figure 10A:
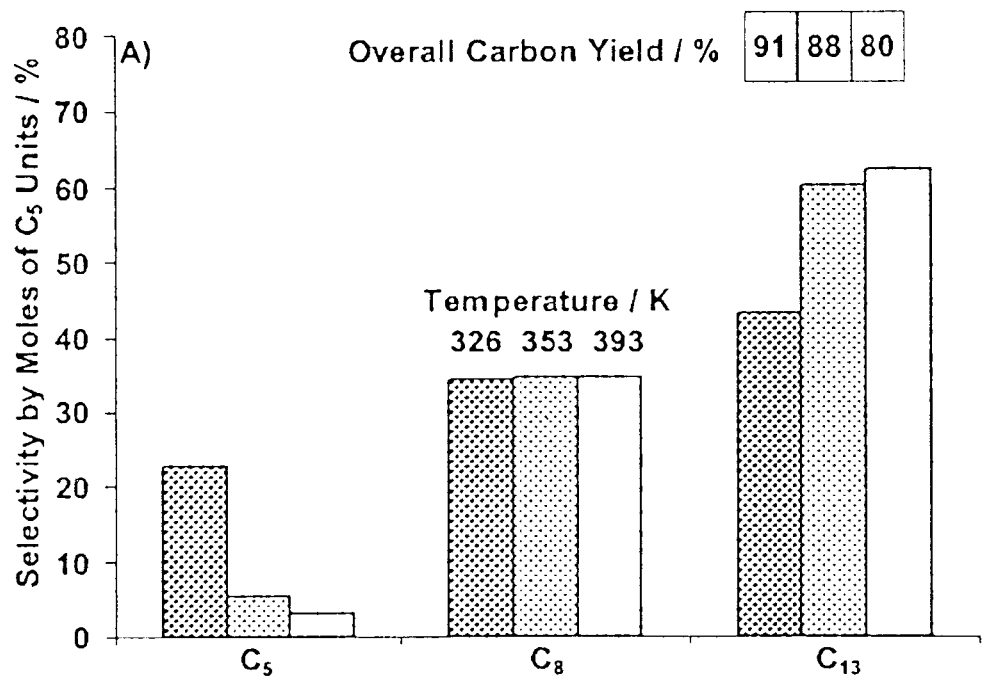
FIGS. 10A and 10B are histograms depicting selectivity based on $C_5$ (furfural:acetone) or $C_6$ (HMF:acetone) units in the aqueous phase after aldol condensation followed by hydrogenation over 5 wt % Pd/MgO—$ZrO_2$ catalyst.

FIG. 10A (Table 4, runs 1, 5, 6) shows experimental results obtained at reaction temperatures from 298 to 393 K for aldol condensations of furfural with acetone at a molar ratio of 1:1. The rate of reaction increases with temperature; however, the overall carbon yield in the aqueous solution after aldol condensation (followed by hydrogenation) decreases at temperatures above 353 K, probably caused by the formation of coke on the catalyst during aldol condensation. As the temperature is increased from 326 to 353 K, the selectivity for dimer increases by 17% with no significant change in the overall carbon yield. In contrast, as the temperature is increased further from 353 to 393 K, the dimer selectivity remains the same but the overall carbon yield decreases by 8%. Thus, it appears that the optimum temperature for aldol condensation of furfural is about 353 K, with this temperature providing a compromise between the selectivity for heavier product and overall carbon yield.

Figure 10B:
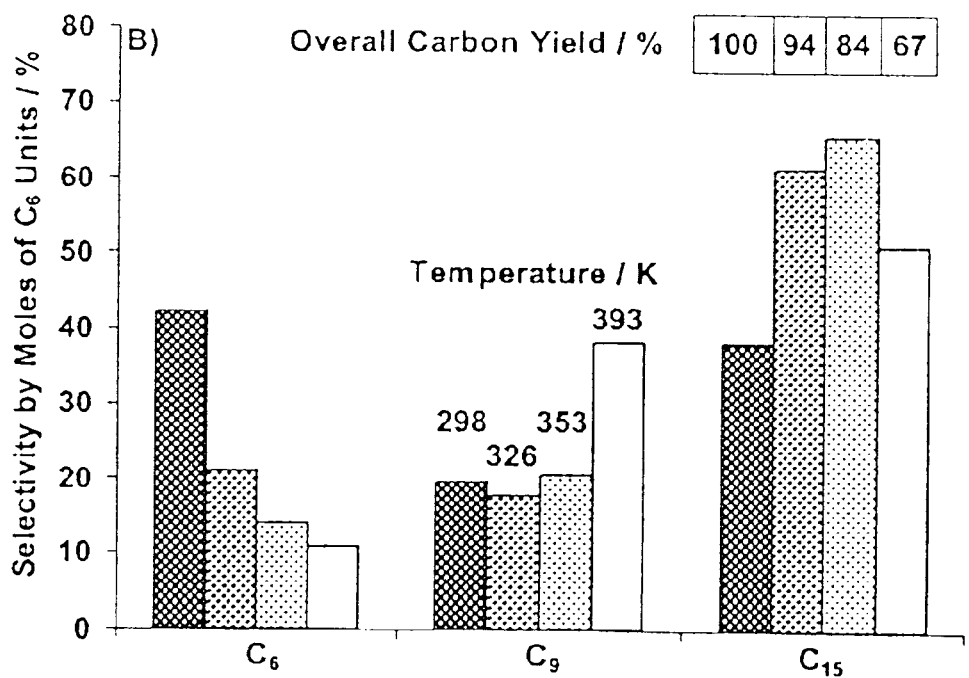

In the case of aldol condensation between HMF and acetone (FIG. 10B; Table 4, runs 14-17), the overall yield of carbon is 67% at 393 K. At lower temperatures, there is a marked increase in selectivity for dimer (increased by 23%) as temperature increased from 298 to 326 K. There was also seen a 10% decrease in overall carbon yield as temperature was increased further from 326 to 353 K. Thus, the temperature trends for HMF and furfural are similar. Accordingly, the optimum temperature for aldol condensation of HMF with acetone is about 326 K. This example shows that the aldol condensation temperature has a significant effect on the selectivity of the reaction and the overall yield of the process, with the optimum temperature for condensation with acetone being higher for furfural compared to HMF. At these optimum temperatures, the furfural:acetone reaction achieves a higher final conversion (by 16%) but a lower dimer-to-monomer ratio (1.8 versus 3.4) as compared to the HMF:acetone reaction.

Figure 11:
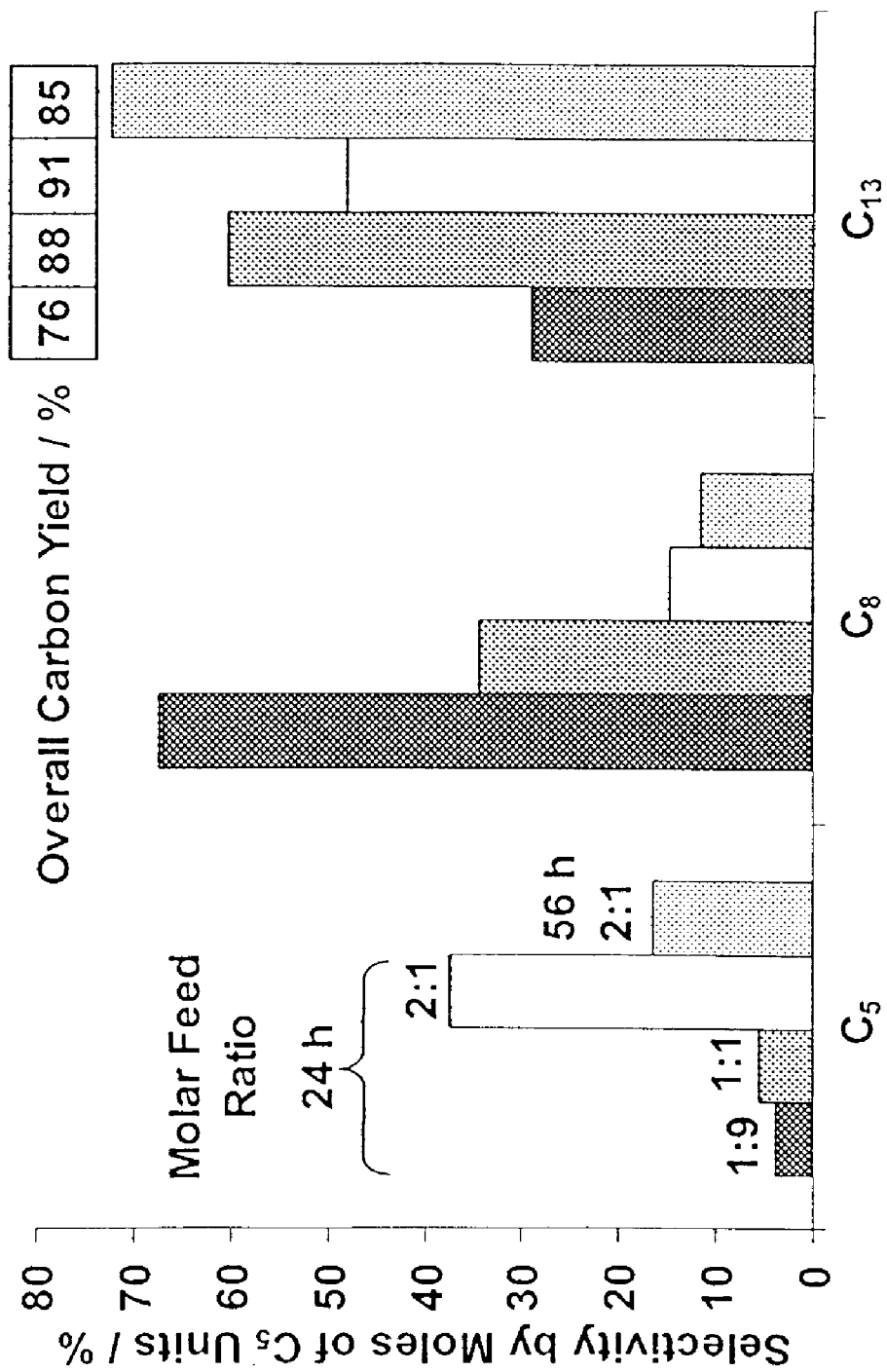
FIG. 11 is a histogram depicting selectivity based on $C_5$ (furfural:acetone) units in the aqueous phase after aldol condensation followed by hydrogenation over 5 wt % Pd/MgO—$ZrO_2$ catalyst. Various furfural:acetone molar ratios were carried out over fresh catalyst at 353 K for condensation followed by hydrogenation at 393 K. From left-to-right, the first three bars in each four-bar group shows condensation for 24 h, while the fourth bar in each four-bar group shows condensation for 56 h.

The results presented in FIG. 11 (Table 4, runs 5, 7-9) show that the molar ratio of reactants for aldol condensation plays a significant role in controlling the reaction selectivity. The presence of excess acetone (furfural:acetone molar ratio of 1:9) leads primarily to the formation of monomer, because it is more probable that a furfural molecule will react with an acetone molecule in contrast to reacting with a monomer species. When the molar ratio of furfural:acetone was increased from 1:9 to 1:1, the selectivity for the formation of dimer species was increased by 31%, and this selectivity increased a further 12% when the furfural:acetone ratio was increased from 1:1 to 2:1. As the furfural:acetone ratio is increased the condensation step requires additional time as shown by an increase in dimer selectivity by 24% when the condensation step is carried out for 56 h instead of 24 h.

Experiments were carried out to study the effects of varying the organic/catalyst ratio, the palladium loading, and of performing the hydrogenation step in hexadecane instead of water. Increasing the organic/catalyst mass ratio from 6 to 36 (Table 4, runs 6, 10, 11) does not have an effect on the selectivity and the overall carbon yield of the process. Decreasing the amount of Pd on the MgO—$ZrO_2$ catalyst from 5 to 0.5 wt % (Table 4, runs 6, 12) increased by about an order of magnitude the time required to reach high overall yields of carbon in the aqueous phase at 393 K (i.e., from about 5 to about 40 h). In Table 4, run 13, the aqueous solution was removed at the end of the aldol condensation step, leaving the insoluble monomer and dimer species on the catalyst surface; and the reactor was then filled with hexadecane, followed by hydrogenation at 393 K. This treatment led to the formation of hydrogenated monomer and dimer species in the hexadecane solvent, with an overall carbon yield of around 71%, indicating that the hydrogenated form of monomer and dimer can be blended with diesel fuel without the need to convert these species into alkanes, thereby eliminating the need for the further APD/H processing step.

The Examples demonstrate that the Pd/MgO—$ZrO_2$ catalyst tested here is an active, selective, and hydrothermally stable catalyst for aldol condensation over basic sites (MgO—$ZrO_2$) followed by sequential hydrogenation over metal sites (Pd). This bifunctional catalytic system thus allows carbohydrate-derived compounds, such as furfural and HMF, to be converted in a single reactor to large water-soluble intermediates for further aqueous phase processing to produce liquid alkanes. The selectivity and overall yield of the process can be controlled by the reaction temperature and the molar ratio of the aldol condensation reactants.

What is claimed is:

1. A method for making alkanes comprising, in an aqueous reaction solution:
  (a) subjecting a carbonyl compound to at least one self-aldol condensation reaction or a crossed-aldol condensation reaction with another carbonyl compound to yield a beta-hydroxy carbonyl compound and/or an alpha-beta unsaturated carbonyl compound; then
  (b) hydrogenating the beta-hydroxy carbonyl and/or alpha-beta unsaturated compounds to yield a saturated polyhydroxy compound; and then
  (c) dehydrating and hydrogenating the saturated polyhydroxy compound to yield a $C_6$ to $C_{15}$ alkane that is immiscible in the aqueous reaction solution.

2. The method of claim 1, wherein step (a) further comprises running the self-aldol condensation reaction or the crossed-aldol condensation reaction in the presence of a catalyst comprising magnesium, zirconium, and oxygen.

3. A method for making alkanes comprising, in an aqueous reaction solution:
  (a) reducing a carbohydrate reactant to yield at least one carbonyl compound having an alpha-position hydrogen; then
  (b) subjecting the carbonyl compound to at least one self-aldol condensation reaction or a crossed-aldol condensation reaction with another carbonyl compound to yield a beta-hydroxy carbonyl compound and/or an alpha-beta unsaturated carbonyl compound; then
  (c) hydrogenating the beta-hydroxy carbonyl and/or the alpha-beta unsaturated carbonyl compounds to yield a saturated polyhydroxy compound; and then
  (d) dehydrating and hydrogenating the saturated polyhydroxy compound to yield an alkane that is immiscible in the aqueous reaction solution.

4. The method of claim 3, wherein in step (a) the carbohydrate reactant is a sugar.

5. The method of claim 3, wherein in step (a), the carbohydrate reactant is derived from biomass.

6. The method of claim 3, wherein step (b) comprises running the self-aldol condensation reaction or the crossed-aldol condensation reaction in the presence of a catalyst comprising magnesium, zirconium, and oxygen.

7. A method for making alkanes comprising, in an aqueous reaction solution:
  (a) dehydrating a $C_6$ sugar to yield hydroxymethylfurfural; then
  (b) subjecting the hydroxymethylfurfural to at least one crossed-aldol condensation reaction with an aldehyde or a ketone to yield a beta-hydroxy carbonyl and/or an alpha-beta unsaturated carbonyl having at least seven (7) carbon atoms; then
  (c) hydrogenating the beta-hydroxy carbonyl and/or alpha-beta unsaturated carbonyl to yield a saturated polyhydroxy compound; and then
  (d) dehydrating and hydrogenating the saturated polyhydroxy compound to yield an alkane having at least seven (7) carbon atoms.

8. The method of claim 7, wherein in step (a), the $C_6$ sugar is derived from biomass.

9. The method of claim 7, wherein step (b) yields a beta-hydroxy carbonyl and/or an alpha-beta unsaturated carbonyl having at least nine (9) carbon atoms; and step (d) yields an alkane having at least nine (9) carbon atoms.

10. The method of claim 7, wherein step (b) yields a beta-hydroxy carbonyl and/or an alpha-beta unsaturated carbonyl having at least eleven (11) carbon atoms; and step (d) yields an alkane having at least eleven (11) carbon atoms.

11. The method of claim 7, wherein step (b) yields a beta-hydroxy carbonyl and/or an alpha-beta unsaturated carbonyl having at least thirteen (13) carbon atoms; and step (d) yields an alkane having at least thirteen (13) carbon atoms.

12. The method of claim 7, wherein step (b) yields a beta-hydroxy carbonyl and/or an alpha-beta unsaturated carbonyl having at least fifteen (15) carbon atoms; and step (d) yields an alkane having at least fifteen (15) carbon atoms.

13. The method of claim 7, wherein step (b) comprises running the self-aldol condensation reaction or the crossed-aldol condensation reaction in the presence of a catalyst comprising magnesium, zirconium, and oxygen.

14. A method for making alkanes comprising, in an aqueous reaction solution:
 (a) dehydrating a $C_6$ sugar to yield hydroxymethylfurfural; then
 (b) hydrogenating the hydroxymethylfurfural to yield hydroxymethyltetrahydrofurfural; then
 (c) subjecting the hydroxymethyltetrahydrofurfural to a self-aldol condensation reaction to yield a $C_{12}$ beta-hydroxy ketone and/or a $C_{12}$ alpha-beta unsaturated ketone; then
 (d) hydrogenating the $C_{12}$ beta-hydroxy ketone and/or the $C_{12}$ alpha-beta unsaturated ketone to yield a saturated polyhydroxy compound; and then
 (e) dehydrating and hydrogenating the saturated polyhydroxy compound to yield a $C_{12}$ alkane.

15. The method of claim 14, wherein step (c) comprises running the self-aldol condensation reaction in the presence of a catalyst comprising magnesium, zirconium, and oxygen.

16. A method for making alkanes comprising, in an aqueous reaction solution:
 (a) dehydrating a $C_6$ sugar to yield hydroxymethylfurfural; then
 (b) subjecting the hydroxymethyltetrahydrofurfural to a first crossed-aldol condensation reaction with a first carbonyl compound having an alpha-position hydrogen, and then a second crossed-aldol condensation reaction with a second carbonyl compound lacking an alpha-position hydrogen, to yield a di-(beta-hydroxy) carbonyl and/or a di-(alpha-beta unsaturated) carbonyl having at least ten (10) carbon atoms; then
 (c) hydrogenating the di-(beta-hydroxy) carbonyl and/or the di-(alpha-beta unsaturated) carbonyl to yield a saturated polyhydroxy compound; and then
 (d) dehydrating and hydrogenating the polyhydroxy compound to yield an alkane having at least ten (10) carbon atoms.

17. The method of claim 16, wherein in step (b) the first carbonyl compound is acetone, and the second carbonyl compound is hydroxymethylfurfural.

18. The method of claim 16, wherein step (b) comprises running the first crossed-aldol condensation reaction and the second crossed-aldol reaction in the presence of a catalyst comprising magnesium, zirconium, and oxygen.

19. A method for making to $C_1$ to $C_{15}$ alkanes comprising, in an aqueous reaction solution:
 (a) subjecting a carbonyl compound to at least one self-aldol condensation reaction or a crossed-aldol condensation reaction with another carbonyl compound to yield a beta-hydroxy carbonyl compound and/or an alpha-beta unsaturated carbonyl compound; then
 (b) hydrogenating the beta-hydroxy carbonyl and/or alpha-beta unsaturated compounds to yield a saturated polyhydroxy compound; and then
 (c) dehydrating and hydrogenating the saturated polyhydroxy compound to yield a $C_1$ to $C_{15}$ alkane.

20. The method of claim 19, wherein step (a) further comprises running the self-aldol condensation reaction or the crossed-aldol condensation reaction in the presence of a catalyst comprising magnesium, zirconium, and oxygen.

21. A method for making alkanes comprising, in an aqueous reaction solution:
 (a) dehydrating a $C_5$ sugar to yield furfural; then
 (b) subjecting the furfural to at least one crossed-aldol condensation reaction with an aldehyde or a ketone to yield a beta-hydroxy carbonyl and/or an alpha-beta unsaturated carbonyl having at least six (6) carbon atoms; then
 (c) hydrogenating the beta-hydroxy carbonyl and/or alpha-beta unsaturated carbonyl to yield a saturated polyhydroxy compound; and then
 (d) dehydrating and hydrogenating the saturated polyhydroxy compound to yield an alkane having at least six (6) carbon atoms.

22. A method for making alkanes comprising, in an aqueous reaction solution:
 (a) dehydrating a $C_5$ sugar to yield furfural; then
 (b) subjecting the furfural to a first crossed-aldol condensation reaction with a first carbonyl compound having an alpha-position hydrogen, and then a second crossed-aldol condensation reaction with a second carbonyl compound lacking an alpha-position hydrogen, to yield a di-(beta-hydroxy) carbonyl and/or a di-(alpha-beta unsaturated) carbonyl having at least nine (9) carbon atoms; then
 (c) hydrogenating the di-(beta-hydroxy) carbonyl and/or the di-(alpha-beta unsaturated) carbonyl to yield a saturated polyhydroxy compound; and then
 (d) dehydrating and hydrogenating the polyhydroxy compound to yield an alkane having at least eight (8) carbon atoms.

23. A method for making alkanes comprising, in an aqueous reaction solution:
 (a) subjecting tetrahydrofurfural to a self-aldol condensation reaction to yield a $C_{10}$ beta-hydroxy ketone and/or a $C_{10}$ alpha-beta unsaturated ketone; then
 (b) hydrogenating the $C_{10}$ beta-hydroxy ketone and/or the $C_{10}$ alpha-beta unsaturated ketone to yield a saturated polyhydroxy compound; and then
 (c) dehydrating and hydrogenating the saturated polyhydroxy compound to yield a $C_{10}$ alkane.

24. A method for making organic polyhydroxy compounds comprising, in an aqueous reaction solution:
 (a) subjecting a carbonyl compound to at least one self-aldol condensation reaction or a crossed-aldol condensation reaction with another carbonyl compound to yield a beta-hydroxy carbonyl compound and/or an alpha-beta unsaturated carbonyl compound; then
 (b) hydrogenating the beta-hydroxy carbonyl and/or alpha-beta unsaturated compounds to yield a polyhydroxy compound.

25. The method of claim 24, wherein in step (b) the beta-hydroxy carbonyl and/or alpha-beta unsaturated compounds are hydrogenated such that the polyhydroxy compound is a saturated polyhydroxy compound.

26. The method of claim 25, further comprising, after step (b):

(c) dehydrating and hydrogenating the saturated polyhydroxy compound to yield a $C_6$ to $C_{15}$ alkane that is immiscible in the aqueous reaction solution.

27. The method of claim 24, further comprising, after step (b):

(c) dehydrating the saturated polyhydroxy compound to yield a $C_6$ to $C_{15}$ alkene or ether.

28. The method of claim 24, wherein step (a) further comprises running the self-aldol condensation reaction or the crossed-aldol condensation reaction in the presence of a catalyst comprising magnesium, zirconium, and oxygen.

* * * * *